(12) United States Patent
Furet et al.

(10) Patent No.: US 6,933,290 B2
(45) Date of Patent: Aug. 23, 2005

(54) 2-{N-(2-AMINO-3-(HETEROARYL OR ARYL)
PROPIONYL)-AMINOACYL}-AMINO}-
ALKYLBORONIC ACID DERIVATIVES

(75) Inventors: Pascal Furet, Thann (FR); Vito Guagnano, Basel (CH); Patricia Imbach, Kaiseraugst (CH); Marc Lang, Mulhouse (FR)

(73) Assignee: Novartis AG, Basel (CH)

( * ) Notice: Subject to any disclaimer, the term of this patent is extended or adjusted under 35 U.S.C. 154(b) by 18 days.

(21) Appl. No.: 10/478,794

(22) PCT Filed: May 29, 2002

(86) PCT No.: PCT/EP02/05937

§ 371 (c)(1),
(2), (4) Date: Nov. 25, 2003

(87) PCT Pub. No.: WO02/096933

PCT Pub. Date: Dec. 5, 2002

(65) Prior Publication Data
US 2004/0167337 A1 Aug. 26, 2004

(30) Foreign Application Priority Data

May 30, 2001 (GB) .............................................. 0113096
Dec. 7, 2001 (GB) .............................................. 0129394

(51) Int. Cl.$^7$ ........................ A61K 31/69; A61K 38/05; C07K 5/06; C07K 5/08
(52) U.S. Cl. ........................ 514/64; 530/331; 549/213; 562/7; 514/18; 514/19
(58) Field of Search ............................. 514/64, 19, 18; 530/331; 549/213; 562/7

(56) References Cited

U.S. PATENT DOCUMENTS

| | | |
|---|---|---|
| 4,499,082 A | 2/1985 | Shenvi et al. |
| 5,106,948 A | 4/1992 | Kinder et al. |
| 5,169,841 A | 12/1992 | Kleeman et al. |
| 5,384,410 A | 1/1995 | Kettner |
| 5,550,262 A | 8/1996 | Iqbal et al. |
| 5,614,649 A | 3/1997 | Iqbal et al. |
| 5,658,885 A | 8/1997 | Lee et al. |
| 5,780,454 A | 7/1998 | Adams et al. |
| 6,066,730 A | 5/2000 | Adams et al. |
| 6,083,903 A | 7/2000 | Adams et al. |
| 6,297,217 B1 | 10/2001 | Adams et al. |
| 2001/0012854 A1 | 8/2001 | Siman et al. |

FOREIGN PATENT DOCUMENTS

| | | |
|---|---|---|
| EP | 145 441 B1 | 6/1985 |
| EP | 315 574 A2 | 5/1989 |
| EP | 471 651 A2 | 2/1992 |
| WO | 94/21668 | 9/1994 |
| WO | 94 25049 | 11/1994 |
| WO | 96 12499 | 5/1996 |

OTHER PUBLICATIONS

Adams, J. et al.: Potent and selective inhibitors of the proteasome: dipeptidyl boronic acids. Bioorg. & Medicin. Chem. Lett. vol. 8, pp. 333–338, 1998.*

Proteasome Inhibitor Program, Cephalon, Inc., Jul. 2001.

Internal Search Memo by Vera Stanek, Jan. 11, 2002.

Adams, Julian et al., "Potent and selective inhibitors of the proteasome: dipeptidyl boronic acids," Bioorganic & Medicinal Chemistry Letters 8(4), pp. 333–338 (1998), Missing BR, BS.

Christie, G, et al., "Alzheimer's disease: correlation of the suppression of .beta.–amyloid peptide secretion from cultured cells with inhibition of the chymotrypsin–like activity of the proteasome," Journal of Neurochemistry, 73(1), pp. 195–204 (1999), Missing BR, BS.

\* cited by examiner

*Primary Examiner*—Charanjit S. Aulakh
(74) *Attorney, Agent, or Firm*—Lydia T. McNally

(57) ABSTRACT

Disclosed are derivatives of 2-{[N-(2-amino-3-(heteroaryl or aryl)propionyl)-aminoacyl]-amino}-alkylboronic acid, processes for the preparation of such compounds, pharmaceutical preparations, and the use of such derivatives in the preparation of pharmaceutical compositions for the therapeutic treatment of warm-blooded animals, including humans 18 Claims, No Drawings

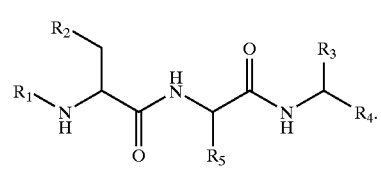

(I)

2-{N-(2-AMINO-3-(HETEROARYL OR ARYL) PROPIONYL)-AMINOACYL}-AMINO}-ALKYLBORONIC ACID DERIVATIVES

The invention relates to 2-{[N-(2-amino-3-(heteroaryl or aryl)propionyl)-aminoacyl]-amino}-alkylboronic acid derivatives, to processes for the preparation thereof, to pharmaceutical preparations comprising those compounds, and to the use thereof in the preparation of pharmaceutical compositions for the therapeutic treatment of warm-blooded animals, including humans.

The invention relates to compounds of formula I

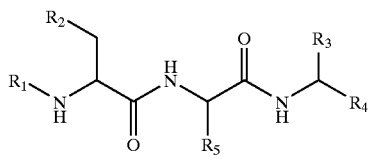

(I)

wherein
$R_1$ is unsubstituted or substituted aryl; arylalkylcarbonyl, wherein the aryl moiety is unsubstituted or substituted; unsubstituted or substituted heterocyclyl; or heterocyclylalkylcarbonyl, wherein the heterocyclyl moiety is unsubstituted or substituted;
$R_2$ is unsubstituted or substituted aryl or unsubstituted or substituted heteroaryl;
$R_3$ is hydrogen, unsubstitued or substituted aryl or alkyl which is unsubstituted or substituted by
unsubstituted or substituted cycloalkyl,
unsubstituted or substituted aryl, or
unsubstituted or substituted heteroaryl comprising at least one nitrogen atom;
$R_4$ is a moiety of the formula IA,

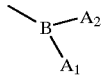

(IA)

wherein $A_1$ and $A_2$ are hydroxy or substituted hydroxy, or together with the binding boron atom and the two binding oxygen atoms form a ring of the formula IA*,

(IA*)

wherein W is alkylene, substituted alkylene, unsubstituted or substituted cycloalkylene, unsubstituted or substituted bicycloalkylene or unsubstituted or substituted tricycloalkylene;
and $R_5$ is unsubstituted or substituted alkyl, unsubstituted or substituted aryl, unsubstituted or substituted heterocyclyl, or unsubstituted or substituted cycloalkyl;
or salts thereof.

Within the context of the present disclosure the general terms used hereinbefore and hereinafter preferably have the following meanings:

Aryl preferably has a ring system of not more than 20 carbon atoms, especially not more than 12 carbon atoms, is preferably mono-, bi- or tric-cyclic, and is unsubstituted or substituted, preferably in each case unsubstituted or substituted phenyl or (especially 1- or 2-)naphthyl, one or more substituents preferably being independently selected from the group consisting of an aliphatic radical; free, etherified or esterified hydroxy; free or esterified carboxy; formyl; alkanoyl; unsubstituted, mono- or di-substituted amino; mercapto; sulfo; alkyl-thio; carbamoyl; N-alkyl-carbamoyl; N,N-di-alkyl-carbamoyl; phenyl; naphthyl; heterocyclyl, especially pyridyl; cyano and nitro, more preferably being selected from alkyl, e.g. methyl, ethyl or propyl; alkoxy, e.g. methoxy or ethoxy; di-substtuted amino, e.g. dimethylamino; halogen, e.g. chloro or bromo; halogen-alkyl, e.g. trifluoromethyl; and phenyl, (especially 1- or 2-)-naphthyl, and heterocyclyl, especially as defined below, especially pyridyl, e.g. 3-, 4- or especially 2-pyridyl, each of which is unsubstituted or substituted with one or more, especially up to three, substituents, especially independently selected from the other aryl substitutents just mentioned. Aryl $R_1$ is more preferably biphenylyl, especially 2-, 4- or preferably 3-biphenylyl, pyridylphenyl, especially 4-, 3- or most especially 2-pyridyl-(2-, 4- or preferably 3-)phenyl, or lower alkyl-phenyl, especially propyl-phenyl, such as 2-, 4- or especially 3-isopropylphenyl. Arylalkylcarbonyl $R_1$ (with unsubstituted or preferably substituted aryl) is preferably aryl-lower alkylcarbonyl with aryl as defined above, more preferably phenyl-lower alkyloxy-phenyl-lower alkylcarbonyl, especially 2-, 4- or preferably 3-benzyloxyphenyl-acetyl or -propionyl, pyridyl-lower alkyloxyphenyl-lower alkylcarbonyl, especially 2-, 4- or preferably 3-(pyridin-2-, 4- or preferably -3-)-acetyl or -propionyl, or phenyl-lower alkylcarbonyl, especially phenyl-2- or preferably 3-phenyl-propionyl or phenylacetyl, wherein phenyl is unsubstituted or substituted by up to three substitutents independently selected from lower alkoxy, especially methoxy, halogen, especially fluoro or chloro, or halogen-lower alkyl, such as trifluoromethyl. Unsubstituted or substituted aryl $R_2$ or (independently) $R_3$ is preferably mono-, di- or trisubstituted phenyl, especially substituted by up to four substituents independently selected from the substitutents mentioned for aryl, especially from hydroxy, lower alkoxy (most preferred), preferably methoxy, halogen, preferably fluoro or chloro, and halogen-lower alkyl, preferably trifluoromethyl, especially phenyl substituted by up to three lower alkoxy, preferably methoxy, substituents, or in case of $R_3$ unsubstituted phenyl, or further unsubstituted or substituted napthyl, especially 1- or 2-naphthyl that is unsubstituted or substituted by up to four substituents independently selected from the substitutents mentioned for aryl, especially from hydroxy, lower alkoxy (most preferred), preferably methoxy, halogen, preferably fluoro or chloro, and halogen-lower alkyl, preferably trifluoromethyl.

Unsubstituted heterocyclyl is preferably a heterocyclic radical that is unsaturated, saturated or partially saturated in the bonding ring and is preferably monocyclic or in a broader sense bicyclic or tricyclic ring; has 3 to 24, more preferably 4 to 16 ring atoms; wherein at least in the ring bonding to the radical of the molecule of formula I one or more, preferably one to four, especially one or two carbon atoms of a corresponding aryl radical are substituted by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above as substituents of substituted aryl; and especially being a heteroaryl radical selected from the group consisting of imidazolyl, thienyl, furyl, tetrahydrofuryl, pyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazolidinyl, pyranyol, thiazolyl, isothiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, indolyl, indazolyl, triazolyl, tetrazolyl, purinyl, 4H-quinolizinyl, isoquinolyl, quinolyl, tetrahydroquinolyl, tetrahydroisoqionolyl, decahydroquinolyl, octahydroisoquinolyl, benzofuranyl, benzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, isochromanyi and chromanyl, each of these radicals being unsubstituted or substituted by one to two radicals selected from the group consisting of lower alkyl, especially methyl or tert-butyl, lower alkoxy, especially methoxy, and halo, especially bromo or chloro; pyridyl, especially 2- or 3-pyridyl, or indolyl is especially preferred, in a broader aspect lower alkyl-pyridyl, pyrimidinyl or lower alkylpyrimidinyl, halo-lower alkylpyridyl, lower alkoxy-pyridyl, di-lower alkyl-pyridyl, or halo-pyridyl. Heterocyclyl is unsubstituted or substituted by one or more, preferably up to three, substitutents independently selected from those mentioned above for aryl (where heterocyclyl as substituent of heterocyclyl carries no further heterocyclyl substituent other than pyridyl or indolyl) and from aryl as defined above, especially phenyl, especially those mentioned as being preferred. Unsubstituted heterocyclyl is preferred.

In heterocyclylalkylcarbonyl $R_1$, the heterocyclyl moiety is preferably substituted or especially unsubstituted heterocyclyl as mentioned above; preferred is substituted or preferably unsubstituted heterocyclyl-lower alkyl, especially with terminal substituted or preferably unsubstituted heterocyclyl, with heterocyclyl as described above; preferred is pyridyl-lower alkylcarbonyl, such as -acetyl or -propionyl.

As $R_1$, unsubstituted or substituted aryl or substituted aryl-lower alkylcarbonyl is preferred over the other meanings.

Heteroaryl $R_2$ is preferably unsubstituted or substituted heteroaryl as mentioned above, especially indolyl that is unsubstituted or substituted by one or more, especially up to three, substitutents independently selected from those mentioned above for substituted aryl, especially from hydroxy, lower alkoxy (most preferred), preferably methoxy, halogen, preferably fluoro or chloro, and halogen-lower alkyl, preferably trifluoromethyl.

$R_2$ is preferably substituted aryl.

An aliphatic radical preferably has up to 12 carbon atoms, preferably up to 7 carbon atoms, most preferably up to 4 carbon atoms, and is an aliphatic hydrocarbon radical, that is to say such an unsubstituted or substituted alkynyl, alkenyl or preferably alkyl radical, more preferably lower alkyl, especially methyl, ethyl, n-propyl, iso-propyl, n-butyl, sec-butyl, iso-butyl or tert-butyl.

Alkyl, which may be branched or linear, preferably has up to 12 carbon atoms, and is more preferably lower alkyl. Alkyl $R_3$ is preferably lower alkyl, especially isobutyl.

The prefix "lower" denotes a radical having up to and including 7, preferably up to and including 4, carbon atoms.

Lower alkyl is, preferably, n-propyl, isopropyl, n-butyl, isobutyl, sec-butyl, tert-butyl, n-pentyl, isopentyl, neopentyl, n-hexyl or n-heptyl, preferably isobutyl, sec-butyl, tert-butyl, isopropyl, ethyl or methyl, most preferably isopropyl, ethyl or methyl.

Etherified hydroxy is, for example, alkoxy, especially lower alkoxy, such as ethoxy or methoxy, aryloxy, especially phenyloxy, aryl-lower alkoxy, especially phenyl-lower alkoxy, heterocyclyloxy, especially pyridyloxy, or heterocyclyl-lower alkoxy, especially pyridyl-lower alkoxy (aryl and heterocyclyl preferably have the meanings given above).

Esterified hydroxy is preferably hydroxy esterified by an organic carboxylic acid, such as an alkanoic acid, for example lower alkanoyloxy.

Esterified carboxy is, for example, alkoxycarbonyl, especially lower alkoxycarbonyl, such as e.g. methoxycarbonyl.

Mono- or di-substituted amino is, preferably, N-alkylamino or N,N-dialkylamino, especially N-lower alkylamino or lower N,N-di-lower alkylamino, such as N-methylamino or N,N-dimethylamino.

Halogen is fluorine, chlorine, bromine or iodine, preferably fluorine, chlorine or bromine.

Unsubstituted or substituted cycloalkyl preferably has up to 12, more preferably 3 to 8 ring carbonyl atoms and is substituted by one or more, especially up to three, substitutents independently selected from those mentioned for substituted aryl, or preferably unsubstituted. Preferred is cyclopentyl, cyclohexyl or cycloheptyl.

In alkyl $R_3$ substituted with unsubstituted or substituted cycloalkyl, alkyl is preferably as defined above, more preferably lower alkyl, especially isopropyl, and is (preferably terminally) substituted by cycloalkyl as defined above.

In alkyl $R_3$ substituted with unsubstituted or substituted aryl, alkyl is preferably as defined in the last paragraph, and aryl is defined as above and is substituted by one or more, especially up to three, substitutents independently selected from those mentioned for substituted aryl, or unsubstituted; especially aryl is phenyl substituted by one or more, especially up to three, substitutents independently selected from halogen, especially fluoro, hydroxy or lower alkoxy, especially methoxy, or it is unsubstituted phenyl.

In alkyl $R_3$ substituted with unsubstituted or substituted heterocyclyl, alkyl is preferably as defined for alkyl $R_3$ substituted with cycloalkyl, and heterocyclyl is defined as above and is substituted by one or more, especially up to three, substitutents independently selected from those mentioned for substituted heterocyclyl, or unsubstituted.

If $A_1$ and $A_2$ each are substituted hydroxy, then substituted hydroxy is preferably alkyloxy, especially lower alkyloxy, aryloxy, especially with unsubstituted or substituted aryl as defined above, or cydloalkyloxy with unsubstituted or substituted cycloalkyl as defined above.

If $A_1$ and $A_2$ together with the binding boron atom and oxygen atoms form a ring or the formula IA* shown above, then W preferably carries the two oxygen atoms bound to the boron atom on two different carbon atoms that are spatially nearby or neighbouring carbon atoms, especially in vicinal ("1,2-") or in "1,3"-position (relatively to each other).

Alkylene is preferably an unbranched $C_2$–$C_{12}$-, preferably $C_2$–$C_7$alkylene moiety, e.g. ethylene, or propylene, in a broader aspect butylene, pentylene or hexylene, bound via two different carbon atoms as just described, preferably vicinal or in "1,3"-position. One or more, especially one, of the carbon atoms not bound to the oxygen atoms binding to the boron atom may be replaced by a heteroatom selected from O, S or preferably N (carrying the required number of H atoms, respectively), for example in 1,5-(3-aza-pentylene).

Substituted alkylene is preferably an unbranched lower alkylene moiety as defined above which is subsituted or unsubstituted by one or more, especially up to three, substituents preferably independently selected from lower alkyl, such as methyl or ethyl, e.g. in 1-methylethylene, 1,2-dimethylethylene, hydroxy, e.g. in 2-hydroxy-propylene, or hydroxy-lower alkyl, such as hydroxymethyl, e.g. in 1-hydroxymethyl-ethylene.

Unsubstituted or substituted cycloalkylene is preferably $C_3$–$C_{12}$-, more preferably $C_3$–$C_8$-cycloalkylene bound via two different carbon atoms as described for W, preferably vicinal or in "1,3"-position, such as cyclohexylene or cyclopentylene, in which one or more, especially one, of the carbon atoms not bound to the oxygen atoms binding to the boron atom may be replaced by a heteroatom selected from O, S or N (carrying the required number of H atoms, respectively), for example in tetrahydrofurylene or tetrahydropyranylene, and may be unsubstituted or substituted by one or more, especially up to three substituents independently selected from lower alkyl, such as methyl or ethyl, hydroxy, hydroxy-lower alkyl, such as methoxy, or mono- or oligosaccharidyl bound via an oxyygen atom ("oligosacchaddyl" preferably comprising up to five saccaridyl moieties).

Unsubstituted or substituted Bicycloalkylene is preferably $C_5$–$C_{12}$-bicycloalkylene bound via two different carbon atoms as described for W, preferably vicinal or in "1,3"-position, in which one or more, especially one, of the carbon atoms not bound to the oxygen atoms binding to the boron atom may be replaced by a heteroatom selected from O, S or N (carrying the required number of H atoms, respectively), and may be unsubstituted or substituted by one or more, especially up to three substituents independently selected from lower alkyl, such as methyl or ethyl, hydroxy and hydroxy-lower alkyl, such as methoxy. Preferred is pinanylene (2,3-(2,6,6-trimethyl-bicyclo[3.1.1]heptane).

Unsubstituted or substituted tricycloalkylene is preferably $C_8$–$C_{12}$-tricycloalkylene bound via two different carbon atoms as described for W, preferably vicinal or in "1,3"-position, in which one or more, especially one, of the carbon atoms not bound to the oxygen atoms binding to the boron atom may be replaced by a heteroatom selected from O, S or N (carrying the required number of H atoms, respectively), and may be unsubstituted or substituted by one or more, especially up to three substituents independently selected from lower alkyl, such as methyl or ethyl, hydroxy and hydroxy-lower alkyl, such as methoxy.

Most preferably, $R_4$ is —$B(OH)_2$ or 2,9,9-trimethyl-3,5-dioxa-4-bora-tricyclo[$6.1.1.0^{2,6}$]dec-4-yl, especially (1S,2S,6R,8S)-2,9,9-trimethyl-3,5-dioxa-4-bora-tricyclo[$6.1.1.0^{2,6}$]dec-4-yl.

In unsubstituted or substituted alkyl $R_5$, alkyl, which may be branched or linear, preferably has up to 12 carbon atoms, and is more preferably lower alkyl. Alkyl $R_5$ is preferably lower alkyl, especially isopropyl. Substituents, of which one or more, especially up to two, may be present, are independently selected from unsubstituted or substituted aryl (especially phenyl or hydroxyphenyl), unsubsituted or substituted heterocyclyl (especially imidazolyl or indolyl), unsubstituted or substituted cycloalkyl, each as defined above; hydroxy (preferred), carboxy (preferred), carbamoyl, mercapto, lower alkylthio, e.g. methylthio, phenyl, hydroxyphenyl, indolyl, imidazolyl, amino, tri-lower alkylamino, e.g. trimethylamino, lower alkanoylamino, e.g. acetylamino, guanidino, N-lower alkylguanidino, e.g. N-methylguanidino, or any other substituent completing an amino acid comprising $R_5$. Preferably, $R_6$ may be methyl, isopropyl, isobutyl, sec-butyl, mercaptomethyl, 2-methylthioethyl, phenylmethyl, hydroxyphenylmethyl, indol-3-ylmethyl, hydroxymethyl, 1-hydroxyethyl, 2-hydroxyethyl, carbamoylmethyl, 2-carbamoylethyl, 4-aminobutyl, 3-guanidinopropyl, 5-imidazolylmethyl, carboxymethyl or 2-carboxyethyl.

Asymmetric carbon atoms of a compound of formula I that are present may exist in the (R), (S) or (R,S) configuration, preferably in the (R) or (S) configuration, most preferably in the configuration indicated in formula I* below. Substituents at a double bond or a ring may be present in cis-(=Z-) or trans (=E-) form. The compounds may thus be present as mixtures of isomers or preferably as pure isomers.

Salt-forming groups in a compound of formula I are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds of formula I having acidic groups, for example a free boronic acid group (—$B(OH)_2$, that is, in formula IA* $A_1$ and $A_2$ each are hydroxy) or a carboxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of saltsa are possible.

Compounds of formula I having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

Owing to the close relationship between the novel compounds in free form and in the form of their salts, including those salts that can be used as intermediates, for example in the purification of the novel compounds or for the identification thereof, any reference hereinbefore and hereinafter to the free compounds shall be understood as including the corresponding salts, where appropriate and expedient.

Where compounds or salts are mentioned, this is meant to include also the singular (one compound or salt).

The compounds of formula I have valuable pharmacological properties and can be used, for example, as drugs to treat proliferative diseases.

The compounds of formula I inhibit the proteasome activity. It is known that proteins targeted for the degradation by the multicatalytic proteasome complex have inter alia functions in the cell-cycle control (e.g. cyclins, p21, p27) and apoptosis (e.g. p53) (Rolfe, M., Chiu, I. M. and Pagano, M., The ubiquitin-mediated proteolytic pathway as therapeutic area. J. Mol. Med. 75, 1997, 5–17). Inhibitors of the proteasome are therefore suitable for the treatment of proliferative diseases which respond to the inhibition of the proteasome activity. Proliferative diseases like psoriaris and tumors, in particular solid tumors like colon tumor, breast tumor, lung tumor and prostate tumor belong to the diseases to be mentioned here. Other proliferative diseases to be treated are psoriasis or restenosis. Also further diseases can be treated in a broader aspect of the invention, e.g. muscle protein degradation or other diseases connected with intracellular protein degradation or negaive nitrogen balance, e.g. in patients suffering from sepsis, burns, trauma, cancer, chronic or systemic infections, neuromotor degenerative disease, e.g. muscular dystrophia, acidosis, spinal or nerve injuries, during corticosteroid treatment, or the like;, diseases related to antigen presentation on cells; diseases related to cell adhesion; or the like, especially as far as proteasome inhibition is effective.

Inhibition of 20S Proteasome

The compounds of formula I inhibit the 20S proteasome, especially with high selectivity the chymotrypsin-like activity.

The multicatalytic proteasome complex is responsible for the ATP-dependent proteolysis of most cellular proteins. Although the 20S proteasome contains the proteolytic core, it cannot degrade proteins in vivo unless it is complexed with 19S caps, at either end of its structure, which itself contains multiple ATPase activities. This larger structure is known as the 26S proteasome and will rapidly degrade proteins that have been targeted for the degradation by the addition of multiple molecules of the 8.5 kDa polypeptide ubiquitin. As mentioned above, proteins targeted for proteasomal degradation have functions in the cell-cycle. The compounds of formula I are therefore highly suitable for the treatment of diseases which respond to inhibition of the activity of the 20S proteasome, which is the case for the proliferative diseases (or further the other diseases) mentioned above.

The inhibition of the chymotrypsin-like activity of the 20S proteasome can be demonstrated by the following experiment. It is based on the hydrolysis of the fluorogenic peptide Suc-LLVY-AMC (Succinyl-leucine-leucine-vatine-tyrosine-7-amino-4-methyl-coumarin), which is cleaved exclusively at the Y-AMC bond by the 20S proteasome. Hydrolysis of this peptide is accompanied by an increase in fluorescence intensity ($\lambda_{ex}$ (excitation wavelength): 355 nm; $\mu_{em}$ (emission wavelength): 460 nm) due to release of the internally quenched 2-aminobenzoyl fluorescence that accompanies diffusion apart of the hydrolysis product Suc-LLVY.

2 μl of a 1 mM solution of a test compound in DMSO (dimethylsulfoxide, 20 μM final concentration in the well) are preincubated for 60 min at room temperature in black 96-well microtiter plates together with a mixture of 1 μl purified human placenta 20S proteasome (Diabetes Forschungsinstitut, Düsseldorf, Germany; about 100 ng proteasome, depending on the proteasome preparation) and 47 μl buffer-Ca (5 mM $CaCl_2$, 20 mM Tris/HCl (Tris-(hydroxymethyl)-amino-methane hydrochloride) pH 8.0). 3 μl of a 2.67 mM solution of Suc-LLVY-AMC (Bachem, Switzerland) in DMSO (80 μM final concentration in the well) and 47 μl buffer-Ca are mixed and added. The resulting mixture is incubated for 3–24 h at 37° C. If desired, proteolysis of the substrate can be stopped by addition of 50 μl stop solution (100 mM monochloroacetic acid, 130 mM NaOH, 100 mM acetic acid, pH=4.3). The fluorescence is monitored with a FLUOROSKAN ASCENT™ microtiter plate reader.

For each measurement series two control experiments are carried out:

1.) 0% value: 2 μl DMSO are used in the above described assay instead of 2 μl of a 1 mM solution of a test compound in DMSO and 48 μl buffer-Ca instead of a mixture of 47 μl buffer-Ca and 1 μl purified proteasome.

2.) 100% value: in the above described assay 2 μl DMSO are used instead of 2 μl of a 1 mM solution of the test compound in DMSO.

Calculation $$\% \text{ remaining activity} = \frac{(\text{value with compound} - 0\% \text{ value})}{(100\% \text{ value} - 0\% \text{ value})} \cdot 100\%$$

The $IC_{50}$ value is defined as that concentration of a compound at which the remaining activity is 50% compared to the 0% control. Compounds of formula I exhibit an $IC_{50}$ value for the inhibition of the chymotrypsin-like activity of the 20S proteasome in the range of between 0.3 nM and 1 μM, especially between 0.5 nM and 200 nM.

On the other hand, the compounds according to the invention are highly specific for the chymotrypsin-like activity.

The inhibition of the trypsin-like (TrpL) activity and the peptidoglutamyl-hydrolyzing (PGPH) activity of the 20S proteasome can be demonstrated by monitoring the hydrolysis of the fluorogenic peptides Boc-LRR-AMC (Boc-leucine-arginine-arginine-7-amino-4-methyl-coumarin) for the TrpL activity and the hydrolysis of Z-LLE-AMC (Z-leucine-leucine-glutamate-7-amino-4-methyl-coumarin) for the PGPH activity. The peptides are cleaved exclusively at the amino acid-AMC bond by the corresponding proteolytic activity of the 20S proteasome. Hydrolysis of the peptides is accompanied by an increase in fluorescence intensity ($\lambda_{ex}$=355 nm, $\lambda_{em}$=460 nm) caused by the release of the internally quenched 2-aminobenzoyl fluorescence, as already described.

2 μl of a 1 mM solution of a test compound in DMSO (dimethylsulfoxide, 20 μM final concentration in the well) are preincubated for 60 min at room temperature in black 96-well microtiter plates together with a mixture of 1 μl human 20S proteasome (about 100 ng proteasome purified from human erythrocytes as described by Dahlmann et al., Biochem. J. 309, 195–202 (1995) and McGuire et al., Biochim. Biophys. Acta 995(2), 181–186 (1989)) and 47 μl buffer-Ca (5 mM $CaCl_2$, 20 mM Trs/HCl (tris (hydroxymethyl)-amino-methane hydrochloride) pH 8.0). 3 μl of a 2.67 mM solution of Suc-LLVY-AMC (Bachem, Switzerland) in DMSO (80 μM final concentration in the well) and 47 μl buffer-Ca are mixed and added for assaying ChyL activity. 3 μl of a 1.67 mM solution of Boc-LRR-AMC (Affinity, Mamhead, UK) in DMSO (50 μM final concentration in the well) or 3 μl of a 3.67 mM solution of Z-ILE-AMC (Calbiochem/Juro Supply AG, Luceme, Switzerland) in DMSO (80 μM final concentration in the well) and 47 μl buffer-Ca are mixed and added for assaying TryL or PGPH activity, respectively. The resulting mixture is incubated for 3 to 24 h at 37° C. If desired, proteolysis of the substrate can be stopped by addition of 50 μl stop solution (100 mM monochloroacetic acid, 130 mM NaOH, 100 mM acetic acid, pH=4.3). The fluorescence is monitored with a FLUOROSKAN ASCENT™ microtiter plate reader.

To each measure series two control experiments have to be carried out:
1) 0% value: 2 µl DMSO are used in the above described assay instead of 2 µl of a 1 mM solution of a test compound in DMSO and 48 µl buffer-Ca instead of a mixture of 47 µl buffer-Ca and 1 µl purified proteasome.
2) 100% value: in the above described assay 2 µl DMSO are used instead of 2 µl of a 1 mM solution of the test compound in DMSO.

Calculation: % remaining activity =

$$\frac{(\text{value with compound} - 0\% \text{ value})}{(100\% \text{ value} - 0\% \text{ value})} \cdot 100\%$$

The $IC_{50}$ value is defined as that concentration of a compound at which the remaining activity is 50%.

In these test systems, the selectivity of the compounds of the formula I for the chymotrypsin-like activity is more than 20-fold, preferably 50 to 3000-fold higher than that for the trypsin-like or peptidoglutamyl-hydrolyzing activity, this selectivity being a further advantage of the compounds of formula I.

The antiproliferative activity of the compounds of formula I can be demonstrated in vitro against e.g. the human breast carcinoma cell line MDA-MB435 (HTB-129) obtained from the American Type Culture Collection (ATCC, Rockville, USA). Routinely the 'CellTiter96™' proliferation assay (Promega, Madison Mich.) is used following the procedure recommended by the supplier. This assay is performed in 96 well plates prepared for tissue culture. Cells are seeded in a density of $2.5 \times 10^4$ per well in 50 µl complete MEM [minimal essential medium] (Gibco-LifeTechnologies) supplemented with 10% fetal calf serum, 100 U/ml PenStrep, 1 mM sodium pyruvate, 4 mM L-Glutamine, 20 mM HEPES and Non Essential Amino Acids. Cells are incubated for 24 hours at 37° C. in humidified atmosphere equilibrated with 5% $CO_2$. Test compounds are added to the cell supernatant as serial dilutions in 50 µl MEM-complete per well. Cells are incubated for at least 48 hours at 37° C. in humidified atmosphere equilibrated with 5% $CO_2$. The tetrazolium dye MTT (3-[4,5-dimethylthiazol-2-yl]-2,5-diphenyltetrazolium bromide) is added to the cell supernatant in a volume of 15 µl per well and cell cultures are incubated for 4 hours. Thereafter, the reaction is stopped by addition of 100 µl stop solution per well and the plates are incubated for one additional hour. The conversion of the tetrazolium dye by metabolically active cells yields soluble formazan. The absorbance of the blue colored cell supernatant is proportional to the amount of viable cells. The absorbance is monitored at the wavelength of 550 and 630 nm using a microtiter plate reader (Dynatech MR5000).

Serial dilutions of compound are prepared by first diluting the 10 mM compound stock solution (in DMSO) to a 60 µM test solution in MEM-complete followed by nine successive 1:3 dilutions in MEM-complete. Wells containing MEM-complete serve as negative control, background (0%). Wells containing cells and MEM/0.6% DMSO serve as positive control (100%). The % remaining activity is determined by calculating as described above for the inhibition of the chymotrypsin-like activity of the 20S proteasome. The $IC_{50}$ value is defined as that concentration of a compound at which the remaining activity is 50%.

Compounds of formula I exhibit an $IC_{50}$ value for the antiproliferative activity in the range of between 0.5 nM and 1 µM, especially between 1 nM and 200 nM.

The antitumoral action of the compounds of formula I can also be demonstrated in vivo:

In vivo Evaluation of Antitumor Action in Nude Mice Using Human Tumor Xenografts Female or male BALB/c nu/nu (Novartis animal farm, Sisseln, Switzerland or Bomholtgaard, Copenhagen, Denmark) mice with subcutaneously transplanted human tumors are used for the evaluation of the antitumor action of the compounds of formula I against cell lines originating from the four tumor types, breast tumor: MCF-7; lung tumor: NCI H596: colon tumor: HCT 116; and prostate tumor: PC 3.

Materials:

Human colon carcinoma HCT 116 (ATCC CCL 247), human squamous cell lung carcinoma NCI H596 (ATCC HTB 178), estrogen-dependent breast carcinoma MCF-7 (ATCC HTB 22), and the human prostate cancer PC 3 cell line are obtained from the American Type Culture Collection (ATCC, Rockville, USA). The cells are cultured at 37° C. in a 5% v/v $CO_2$ and 80% relative humidity atmosphere in the following media: NCl H 596: RPMI 1640, 20% v/v FBS (fetal bovine serum), 1% w/v glutamine; HCT-116: McCoy's 5A, 10% v/v FBS, 1% w/v glutamine; PC 3: RPMI 1640, 20% v/v FBS, 1% w/v glutamine; MCF-7, RPMI 1640, 20% v/v FBS, 1% w/v glutamine. All of these cell lines are adherent and can be released by rinsing with Hank's balanced salt and treatment with 0.25% w/v trypsin. All of these cells are prepared as master cell stocks (in culture media supplemented to contain 20% v/v FBS and 7% v/v DMSO) and stored at −125° C. (liquid nitrogen vapors). Working cell stocks are prepared from the master stocks by thawing and expanding the cells over three passages, which are then distributed to vials and frozen. Viability (trypan blue exclusion test using 0.5% w/v trypan blue) prior to freezing is >90% for all cell lines.

Establishing Solid Tumors in Nude Mice:

Mice are kept under controlled conditions (Optimal Hygienic Conditions, [OHC]) with free access to sterile food and water. Tumors are established after subcutaneous injection of cells (a minimum of $2 \times 10^6$ cells in 100 µl PBS (phosphate buffered saline) or medium) in carrier mice (4–8 mice per cell line). Injections are made s.c. in the left flank of the mouse mid-way between the tail and head. The resulting tumors are serially passaged for a minimum of three consecutive transplantations prior to start of treatment. Tumors are transplanted when the tumor reaches a volume of 800 to 1000 $mm^3$.

Transplanting Solid Tumors in Nude Mice:

Donor mice are anesthetized (Forene®, Abbott, Switzerland) and killed by cervical dislocation. The skin is disinfected and the tumor removed by dissection. The outer edges of the tumor mass is removed using a scalpel, and the resulting mass is trimmed into pieces of about 3–4 mm in height. Sections of 3–4 $mm^2$ are cut and placed into sterile 0.9% w/v NaCl. Sections of tumor that are necrotic are not used.

Tumor fragments are implanted s.c. into the left flank of the recipient mice. Recipient mice are anesthetized (Forene®, Abbott, Switzerland) and the skin on the entire back and sides of the mice is disinfected. The skin 0.5 to 1 cm above the tail is raised and a single 1 to 1.5 cm incision is made. Tumor sections are pushed into a 13-gauge trocar needle. The trocar needle is pushed into the opening of the skin, and advanced under the skin to a point mid-way between the head and the tail. The tumor fragment is deposited by advancing the trocar. The wound is sutured using one or two metal clips.

In the case of estrogen-dependent breast tumors, estrogen pellets (17b-estradiol, 5 mg/pellet giving a sustained release over 60 days are obtained from Innovative Research of America, Sarasota, USA), are placed subcutaneously in the other flank.

The tumors are allowed to increase until the size is 100 to 150 mm$^3$ before treatment is started. The tumors are then measured and placed into groups (normally n=6 to 8) that are balanced according to the mean size and range of tumor volumes. Groups are randomly assigned to treatment groups.
Preparation and Application of Test Compounds:

Stock solutions of 40 mg/ml of compound are dissolved in 100% DMSO and stirred at room temperature until a clear solutions is obtained. Prior to each administration, 10% Tween® 80 (Fluka, Buchs, Switzerland; polyoxyethylene-sorbitane-monostearate; Tween® is a trademark from ICI Americas Inc., USA) is added to the stock solution and then diluted 1:20 (v/v) with sterile 0.9% w/v NaCl or water. Solutions and dilutions are prepared daily prior to application. Applications are given 7 days a week (p.o., i.p., s.c. or i.v.). The volumes of application are: p.o., 25 ml/kg; i.p., 25 ml/kg; s.c., 10 ml/kg; i.v., 10 ml/kg.

Measurement of tumor volumes: Tumor growth is monitored once, twice or three times weekly (depending on the growth rate of the tumor line) and 24 hours after the last treatment by measuring perpendicular diameters. Calipers capable of determining mm distances are used. Tumor volumes are calculated according to the formula L×D$^2$×π/6 (L: length; D: diameter). Antitumor activity is expressed as T/C % (mean increase of tumor volumes of treated animals divided by the mean increase of tumor volumes of control animals multiplied with 100). Tumor regression (%) represents the smallest mean tumor volume compared to the mean tumor volume at the start of treatment. Delta (Δ) tumor volumes compared the change in tumor volume during the duration of the experiment (volume on the last treatment day minus volume on the first treatment day). Any animals in which the tumor reaches a size exceeding approximately 1500 to 2000 mm$^3$ are sacrificed.
Additional Measurements:

Body weights and survival data are also collected. Delta (Δ) body weights are calculated as an indication of tolerability to treatment (weight on the last treatment day—weight on the first treatment day). Statistically significant body weight loss, or mortalities, are considered indicators of poor tolerability to treatment. Additionally, mice are monitored once or twice daily for general health.
Statistical Analyses:

The basic approach for statistical analyses is to use tests for multiple comparisons to judge the statistical significance of differences between treatment groups, and differences within a group to determine if treatment induced stable disease or tumor regressions. As subcutaneous tumor volumes are not always normally distributed, differences in the subcutaneous tumor volumes between treatment groups is determined using the non-parametric Kruskal-Wallis one way ANOVA test on ranked data and the statistical significance of differences between treatment groups as compared to control groups determined using the Dunnett test. Pair wise comparisons between all groups is performed using the Student-Newman-Keuls (SNK) method. If only two groups are compared, the Rank sum test is used. Animal body weights are normally distributed, and changes in body weights within a group are analyzed by paired t-tests and between group differences are analyzed by a One-Way ANOVA and pair-wise comparisons made using the Tukey test. For all tests the level of significance is set at p<0.05.

Using the same methods, instead of the mentioned tumor cell lines also the estrogenin-dependent breast tumor cell line MDA-MB435 (HTB-129), obtainable form the American Type Culture Collection, can be used. Culture of this cell line is in MEM, 10% v/v FBS, 1% w/v glutamine, adherence and release as described above for the other cell lines.

Another in vivo test to determine the antitumoral action of the compounds of formula I is the following hollow fiber assay:
Hollow Fiber Assay: Evaluation of Antitumor Action in Nude Mice In this assay four different human tumors encapsulated in hollow fibers are implantated subcutaneously and/or intraperitonealy into nude mice (athymic female outbred nude mice (Ncr nu/nu)). Animals are then treated with a test compound formulated in an appropriate vehicle, while control animals are treated with the vehicle alone. At the end of the experiment fibers are retrieved, and the number of viable cells is measured using a metabolic assay (MTT, 3-[4,5-dimethylthiazol-2-yl]-2,5-diphenyltetrazolium bromide). Activity of the test compound is measured by comparing the growth of cells in the experimental animals (T) to the growth of cells in the control animals treated with the vehicle alone (C), and is expressed as % T/C.
Materials:

Human colon carcinomas SW 620 and LS 174T, and breast carcinoma MDA-MB-435S are obtained from the American Type Culture Collection (ATCC, Rockville, USA). The colon carcinoma MIP 101, expressing high levels of pgp-1, was originally established from a patient at the Dana Farber Cancer Institute, Boston, USA. All cell lines are grown according to standard tissue culture techniques in RPMI 1640 containing the following additives: 5% FBS (Fetal Bovine Serum), 5 mg/ml insulin, 5 mg/ml transferrin, 5 ng/ml selenous acid, 1 nM β-estradiol, 1 nM testosterone.
Design of the Assay:

The human solid tumor cell lines are encapsulated in PVDF (polyvinylidene fluoride) hollow fibers that are permeable to molecules <500,000 Daltons and that have an inner diameter of 1 mm (Biopore, Spectrum Medical, CA, USA). After encapsulation and prior to implantation into animals, cells are allowed to attach to the inner surface of the fiber by incubation in the tissue culture media for 24 hours. Four hollow fibers are then implanted into one animal intraperitoneally or subcutaneously. In the experimental setup four to six animals are used per group, and the experiment consists of a minimum of three groups:

1. "Time 0" group
2. Control (placebo) group
3. "Treated" (tested compound) group.

Treatment starts 24 hours after implantation of the fibers. Animals are treated once daily, at days 1, 3, and 5. At the same time when the treatment starts, the animals from "Time 0" group are sacrificed, fibers are retrieved, and the number of viable cells at the beginning of the experiment is determined ($T_0$). At day 7 after the implantation all animals are sacrificed, fibers are retrieved, and the number of viable cells is determined for the Control ($C_v$), and for the "Treated" ($T_v$) groups. % T/C is then calculated according to the formula:

$$\% \; T/C = (T_v - T_0)/(C_v - T_0) \times 100\%$$

Encapsulation of Tumor Cells in Hollow Fibers:

Fibers are cut into desired length and soaked for at least 72 h in 70% Ethanol. Afterwards, fibers and instruments for the encapsulation are sterilized. The human solid tumor cell line grown in tissue culture is trypsinized, suspended in a small amount of tissue culture media and transferred into the fibers using a syringe. The fibers are heat sealed and incubated at 37° C. for 24 h in an atmosphere comprising 5% $CO_2$. The fibers are then implanted subcutaneously and/or intraperitonealy into nude mice.

Determination of Viable Cells in Hollow Fibers:

1 g MTT is added to 200 ml PBS (phosphate-buffered saline), stirred for 20 min and filtered (0.22 micron filter). 10 ml of this solution are mixed with 40 ml RPMI 1640 with additives to give the MTT working solution. The retrieved fibers are incubated in 5 ml RPMI 1640 for 30 min at 37° C. in 5% $CO_2$ for stabilization. 0.5 ml of MTT working solution are added to each well of the sample plate. The plates are incubated at 37° C. in 5% $CO_2$ for 4 h. The MTT is aspirated out of each well in the sample plate. 2 ml of 2.5% aqueous protamine sulfate solution is added to each well of the sample plate. The plates are incubated at 4° C. for 24 h. The protamine sulfate is aspirated out of each well in the sample plate. 2 ml of protamine sulfate are added to each well and the plates are incubated at 4° C. for further 24 h. Each fiber is transfered to a well in a 24 well plate. The fibers are cut short allowing them to lie on the bottom of the wells and dried overnight. 250 µl of DMSO are added to each well. The plates are placed on an orbital shaker for 4 h with a cover to protect the MTT from light. 150 µl of each sample are transfered to the appropriate well in a 96 well plate. The plates are read at 540 nm using DMSO as the blanking well.

The bioavaliability after oral administration of compounds of formula I can be shown e.g. in the following test: For peroral administration, a solution of the test substance (25 mg/ml) in a suitable solvent such as Cremophor RH40®/Maisine®/propylene glycol/ethanol (38/32/15/15) is prepared. Female Balb/c mice are fasted for 24 hours prior to the start, and throughout the experiment water is given ad libitum. At various times following drug administration, blood samples are obtained by sacrifycing animals under anaesthesia by curing the vena jugularis, followed by cervical dislocation. Samples are collected in heparinized tubes (typically 0.4–0.6 ml). For sample analysis solid phase extraction and HPLC are used. Drug concentration in the samples is calculated by least-squares linear regression analysis of the peak area ratio (inhibitor/internal standard) of spiked blood standards versus concentration. From the concentration versus time data, the "Area Under the Curve" (AUC) value is calculated by the trapezoidal rule.

Preferred Embodiments of the Invention:

In the following preferred embodiments of the invention, general definitions or expressions can, individually, independently by several or all completely, be replaced with more specific definitions as given above, if not mentioned otherwise, thus defining even more preferred embodiments of the invention.

Preference is given to compounds of formula I, wherein
$R_1$ is either substituted aryl-lower alkylcarbonyl or unsubstituted or substituted aryl,
$R_2$ is substituted aryl or unsubstituted or substituted heterocyclyl,
$R_3$ is lower alkyl, unsubstituted or substituted aryl or lower alkyl which is substituted by unsubstituted or substituted aryl,
$R_4$ is a moiety of the formula IA given above wherein $A_1$ and $A_2$ are hydroxy, lower alkyloxy, aryloxy with unsubstituted or substituted aryl or cycloalkyloxy with unsubstituted or substituted cycloalkyl, or wherein $A_1$ and $A_2$, together with the binding boron atom and the two binding oxygen atoms form a ring of the formula IA* given above wherein W is unsubstituted or substituted lower alkylene bound via two different carbon atoms that are spatially nearby or vicinal, especially in vicinal or, relatively to each other, in "1,3"-position, and
$R_5$ is lower alkyl,
or salts thereof.

More preference is given to compounds of the formula I wherein
$R_1$ is phenyloxyphenyl-lower alkylcarbonyl; phenyl-lower alkoxyphenyl-lower alkyl-carbonyl; pyridyloxyphenyl-lower alkylcarbonyl; phenyl-lower alkylcarbonyl substituted by lower alkoxy, especially methoxy, halogen, especially fluoro or chloro, or halogen-lower alkyl, especially trifluoromethyl; or preferably unsubstituted or substituted phenyl or naphthyl, wherein in both cases the substituents if present are independently one or more, especially one to three, substituents selected from the group consisting of lower alkyl, hydroxy, lower alkoxy, lower alkanoyloxy, carboxy, lower alkoxycarbonyl, formyl, lower alkanoyl, amino, N-lower alkylamino, N,N-di-lower alkylamino, mercapto, sulfo, lower alkyl-thio, carbamoyl, N-lower alkyl-carbamoyl; N,N-di-lower alkyl-carbamoyl, phenyl, naphthyl, pyridyl, cyano and nitro, more preferably lower alkoxy alkoxy, especially methoxy or ethoxy;
$R_2$ is phenyl substituted by one or more, especially one to three, moieties independently selected from the group consisting of hydroxy, lower alkoxy, especially methoxy, halogen, especially fluoro or chloro, and halogen-lower alkyl, especially trifluoromethyl;
$R_3$ is lower alkyl, especially isobutyl, phenyl or phenyl substituted by one or more, especially up to three substituents independently selected from the group consisting of hydroxy, lower alkoxy, especially methoxy, halogen, especially fluoro or chloro, and halogen-lower alkyl, especially trifluoromethyl;
$R_4$ is —B(OH)$_2$ (especially preferred) or or 2,9,9-trimethyl-3,5-dioxa-4-bora-tricyclo[6.1.1.0$^{2,6}$]-dec-4-yl, especially (1S,2S,6R,8S)-2,9,9-trimethyl-3,5-dioxa-4-bora-tricyclo[6.1.1.0$^{2,6}$]dec-4-yl; and
$R_5$ is lower alkyl, especially isopropyl;
or salts thereof.

Preference is given especially to compounds of formula I, wherein
$R_1$ is phenyloxyphenylacetyl, benzyloxyphenylacetyl, pyridyloxyphenylacetyl, biphenylyl, pyridylphenyl, lower alkylphenyl or substituted phenylpropionyloxy wherein the phenyl substituents are up to three substituents independently selected from the group consisting of methoxy, fluoro, chloro and trifluoromethyl;
$R_2$ is phenyl substituted with up to three methoxy substituents, especially 2,3,4-trimethoxyphenyl or 3,4,5-trimethoxyphenyl;
$R_3$ is isobutyl or phenyl that is unsubstituted or substituted with up to three moieties independently selected from hydroxy, fluoro and methoxy;
$R_4$ is (1S,2S,6R,8S)-2,9,9-trimethyl-3,5-dioxa-4-bora-tricyclo[6.1.1.0$^{2,6}$]dec-4-yl or especially —B(OH)$_2$; and
$R_5$ is isopropyl;
or salts thereof.

Preference is further given especially to compounds of formula I, wherein
$R_1$ is biphenylyl, lower alkyl-phenyl, phenyl-lower alkyl-carbonyl, phenoxy-phenyl-lower alkyl-carbonyl, phenyl-lower alkoxy-phenyl-lower alkyl-carbonyl or pyridyl-phenyl;
$R_2$ is either phenyl substituted by 1 to 3 lower alkoxy radicals or phenyl-lower alkoxy-phenyl;
$R_3$ is lower alkyl or phenyl-lower alkyl;
$R_4$ is 4,4,5,5-tetramethyl-[1,3,2]dioxaborolan-2-yl, (1S,2S,6R,8S)-2,9,9-trimethyl-3,5-dioxa-4-bora-tricyclo[6.1.1.0$^{2,6}$]dec-4-yl or —B(OH)$_2$; and
$R_5$ is lower alkyl;
or salts thereof.

Very special preference is given to compounds of formula I or salts thereof, wherein the stereochemistry is as depicted in formula I*

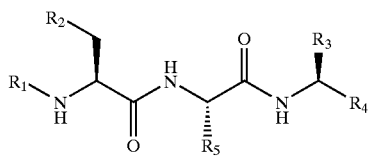
(I*)

wherein the shown configuration represents the absolute configuration and wherein $R_1$, $R_2$, $R_3$, $R_4$ and $R_5$ have the meanings as defined for a compound of formula I, especially those meanings described hereinabove as being preferred.

Also preferred are compounds of formula I or salts thereof, wherein the stereochemistry is as depicted in formula I**

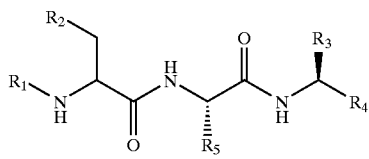
(I**)

wherein the shown configuration represents the absolute configuration and wherein $R_1$, $R_2$, $R_3$, $R_4$ and $R_5$ have the meanings as defined for a compound of formula I, especially those meanings described hereinabove as being preferred.

Further preferred are also compounds of formula I or salts thereof, including mixtures of diastereomers, wherein the stereochemistry is as depicted in formula I***

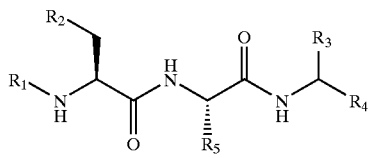
(I***)

wherein the shown configuration represents the absolute configuration and wherein $R_1$, $R_2$, $R_3$, $R_4$ and $R_5$ have the meanings as defined for a compound of formula I, especially those meanings described hereinabove as being preferred.

Most especially preferred are the compounds of formula I described in the Examples, or pharmaceutically acceptable salts thereof.

The compounds of formula I or salts thereof are prepared in accordance with processes known per se, though not previously described for the manufacture of the compounds of the formula I. The processes preferably comprise a) reacting a dipeptide analogue of the formula II,

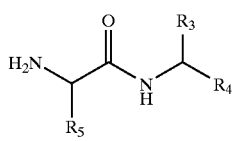
(II)

wherein $R_3$, $R_4$ and $R_5$ have the meanings given under formula I, with an amino acid of the formula III,

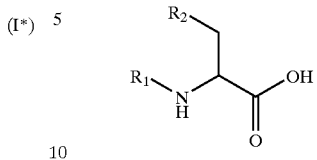
(III)

or a reactive derivative thereof, wherein $R_1$ and $R_2$ have the meanings given under formula I, functional groups present in a compound of formula II and/or III, with the exception of the groups participating in the reaction, being protected if necessary by readily removable protecting groups, and any protecting groups present are removed, or b) for the production of a compound of the formula I wherein $R_1$ is arylalkylcarbonyl or heterocyclylalkylcarbonyl and the other moieties $R_2$ to $R_5$ have the meanings given under formula I, reacting an amino compound of the formula IV,

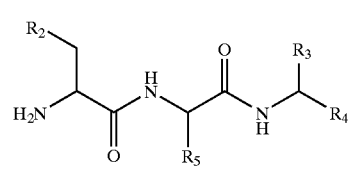
(IV)

wherein $R_2$, $R_3$, $R_4$ and $R_5$ have the meanings given under formula I, with a carbonic acid of the formula V,

(V)

or a reactive derivative thereof, wherein $R_1$ is arylalkylcarbonyl or heterocyclylalkylcarbonyl, functional groups present in a compound of formula IV and/or V, with the exception of the groups participating in the reaction, being protected if necessary by readily removable protecting groups, and any protecting groups present are removed, and, if desired, converting a compound of formula I obtained by process a) or b) into another compound of formula I, converting an obtained free compound of formula I into a salt, converting an obtained salt of a compound of formula I into a different salt or into its free form, and/or separating a mixture of isomeric compounds of formula I into the individual isomers.

The different possible stereoisomers of compounds of formula I can be prepared by using educts with the appropriate configuration. For example, compounds of formula I* or salts thereof can be prepared by a) reacting a dipeptide analogue of the formula II*,

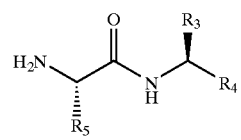
(II*)

wherein $R_3$, $R_4$ and $R_5$ have the meanings given under formula I, with an amino acid of the formula III*,

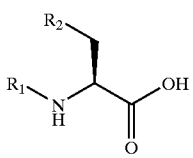
(III*)

or a reactive derivative thereof, wherein $R_1$ and $R_2$ have the meanings given under formula I, functional groups present in a compound of formula II* and/or III*, with the exception of the groups participating in the reaction, being protected if necessary by readily removable protecting groups, and any protecting groups present are removed, or b) for the production of a compound of the formula I* wherein $R_1$ is arylalkylcarbonyl or heterocyclylalkylcarbonyl and the other moieties $R_2$ to $R_5$ have the meanings given under formula I, reacting an amino compound of the formula IV*,

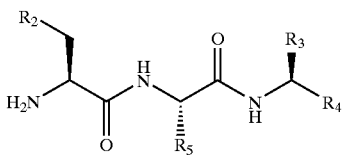
(IV*)

wherein $R_2$, $R_3$, $R_4$ and $R_5$ have the meanings given under formula I, with a carbonic acid of the formula V,

(V)

or a reactive derivative thereof, wherein $R_1$ is arylalkylcarbonyl or heterocyclylalkylcarbonyl, functional groups present in a compound of formula IV* and/or V, with the exception of the groups participating in the reaction, being protected if necessary by readily removable protecting groups, and any protecting groups present are removed, and, if desired, converting a compound of formula I* obtained by process a) or b) into another compound of formula I*, converting an obtained free compound of formula I* into a salt, or converting an obtained salt of a compound of formula I* into a different salt or into its free form.

General Remarks:

The end products of formula I may contain substituents that can also be used as protecting groups in starting materials for the preparation of other end products of formula I, e.g. in the case of $R_4$ other than —$B(OH)_2$. Thus, within the scope of this text, only a readily removable group that is not a constituent of the particular desired end product of formula I is designated a "protecting group", unless the context indicates otherwise.

The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974.

A characteristic of protecting groups is that they can be removed readily (i.e. without the occurrence of undesired secondary reactions) for example by solvolysis, reduction, photolysis or alternatively under physiological conditions (e.g. by enzymatic cleavage).

Removal of a protecting group for the —$B(OH)_2$-group (in order to obtain a compound of the formula I wherein $R_4$ is —$B(OH)_2$) preferably takes place with an acid, e.g. hydrogen chloride, in an appropriate solvent, e.g. a lower alkanol, such as methanol, or a lower alkane, such as hexane, or a mixture thereof, at temperatures of 0 to 50° C., e.g. at room temperature.

Process a):

The reaction is carried out by dissolving the compounds of formulae II and III in a suitable solvent, for example N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and a suitable coupling agent that forms a preferred reactive derivative of the carbonic acid of formula III in situ, for example dicyclohexylcarbodiimide/1-hydroxybenzotriazole (DCC/HOBT); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); or 1-(3-dimethylaminopropyl)-3-ethylcarbodiimide hydrochloride (EDC). For review of other possible coupling agents, see e.g. Klauser; Bodansky, *Synthesis* 1972, 453–463. The reaction mixture is preferably stirred at a temperature of between approximately –20 and 50° C., especially between 0° C. and room temperature, to yield a compound of formula I. The reaction is preferably carried out under an inert gas, e.g. nitrogen or argon.

Process b):

The reaction is preferably carried out under conditions analogous to those described for process a).

Salts of a compound of formula I with a salt-forming group may be prepared in a manner known per se. Acid addition salts of compounds of formula I may thus be obtained by treatment with an acid or with a suitable anion exchange reagent.

Salts can usually be converted to free compounds, e.g. by treating with suitable basic agents, for example with alkali metal carbonates, hydrogencarbonates, or hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallizaton, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Compounds of the formula I wherein $R_4$ is other than —B(OH)$_2$ can be converted into compounds of the formula I wherein $R_4$ is —B(OH)$_2$ according to standard procedures, e.g. using isobutyl-boronic acid (I—BuB(OH)$_2$ in the presence of an acid, especially hydrohalic acid in a water/methanol/hexane mixture, at temperatures preferably ranging from 0 to 50° C., e.g. at room temperature.

In both process a) and b), for the conversion or for the synthesis of the intermediates or starting material, especially as described below, the solvents from which those can be selected which are suitable for the reaction in question include for example water, esters, typically lower alkyl-lower alkanoate, e.g diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitriles, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

New starting materials and/or intermediates, as well as processes for the preparation thereof, are likewise the subject of this invention. In the preferred embodiment, such starting materials are used and reaction conditions selected such as to allow the manufacture of the preferred compounds.

The starting materials of formulae II–V or their precursors are known, can be prepared according to known processes, or are commercially obtainable; in particular, they can be prepared using processes identical or in analogy to those described in the Examples.

A compound of formula II, wherein the substituents are as defined above under formula I, is obtainable for example by the following reactions:

First, a boronic acid analogue of an amino acid of the formula VI

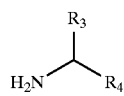

(VI)

comprising for example the configuration as indicated in formula VI*

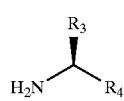

(VI*)

wherein $R_3$ has the meanings given above for compounds of formula I and $R_4$ has the meanings other than —B(OH)$_2$ mentioned above for compounds of formula I, especially is (1S,2S,6R,8S)-2,9,9-trimethyl-3,5-dioxa-4-bora-tricyclo[6.1.1.0$^{2,6}$]dec-4-yl, or an acid addition salt thereof, especially the salt thereof with trifluoroacetic acid, is condensed with an amino acid of the formula VII

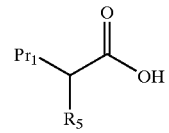

(VII)

comprising for example the configuration as indicated in formula VII*

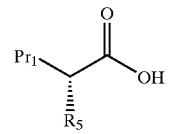

(VII*)

or a reactive derivative thereof, wherein $R_5$ has the meanings given above for compounds of the formula I and $Pr_1$ is a protected amino group, preferably tert-butoxycarbonylamino, under reaction conditions analogous to those described for reaction a) above (also a condensation reaction, also preferably with in situ formation of active carbonic acid derivatives), thus yielding a compound of formula II in N-protected form which is then N-deprotected, e.g. using conditions described in the standard textbooks mentioned above, in the case of tert-butoxycarbonylamino e.g. with hydrochloric acid in an appropriate solvent, e.g. dioxane and/or methylene chloride giving a compound of the formula II that can be used directly in process a).

The boronic acids of the formula VI are known, commercially available and/or can be synthesized according to known procedures. For example, compounds of the formula VI wherein $R_3$ is lower alkyl, especially isobutyl and $R_4$ is as described for compounds of the formula VI, preferably (1S,2S,6R,8S)-2,9,9-trimethyl-3,5-dioxa-4-bora-tricyclo[6.1.1.0$^{2,6}$]dec-4-yl, can be prepared by reacting a compound of the formula VIII,

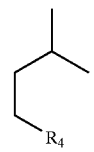

(VIII)

wherein $R_4$ has the meanings just described, in an appropriate solvent, e.g. methylene chloride, with n-lower alkyl lithium, especially n-butyllithium, and subsequently with zinc chloride, yielding a compound of the formula IX,

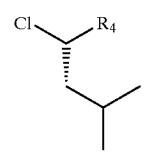

(IX)

wherein $R_4$ has the meanings given above under formula VI. This compound is then reacted with LiN(SiCH$_3$)$_2$, and the resulting compound of the formula is then reacted in the presence of trifluoro acetic acid to yield the salt of the formula X,

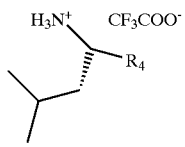

(X)

wherein $R_4$ has the meanings given under formula VI, which is a compound of the formula VI and can then be used directly for reaction with the compound of formula VII as shown above.

A compound of the formula III is known, commercially available and/or can be obtained according to standard procedures.

For example, a compound of the formula III wherein $R_1$ is aryl, especially biphenylyl, may be prepared by reacting a compound of the formula XI,

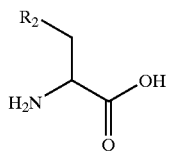

(XI)

comprising for example the configuration as indicated in formula XI*

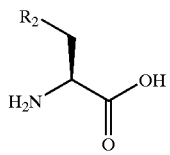

(XI*)

wherein $R_2$ has the meanings given for a compound of the formula I, which is known, commercially available or obtainable according to standard procedures, with a compound of the formula XII, $R_1$—X  (XII)

wherein $R_1$ is aryl and X is halogen, especially bromo, in an appropriate solvent, e.g. in dimethylformamide, in the presence of a base, especially an alkali metal carbonate, e.g. potassium carbonate, at temperatures between 50 and 100° C., e.g. at 90° C., preferably under inert gas, e.g. nitrogen or argon. This directly yields the corresponding compound of the formula III.

Amino acid derivatives of the formula VII are known, commercially available or obtainable according to standard procedures. They are preferably used in the amino protected form, e.g. with tert-butoxycarbonylamino instead of the free amino group.

Compounds of the formula IV can be obtained e.g. by reacting a compound of the formula II comprising for example the configuration as indicated in formula II*, as defined in process a), with an N-protected amino acid of the formula XIII,

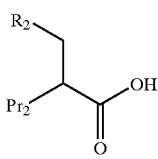

(XIII)

comprising for example the configuration as indicated in formula XIII*

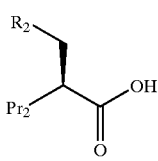

(XIII*)

or a reactive derivative thereof, wherein $R_2$ is as defined under formula I and $Pr_2$ is protected amino, especially tert-butoxycarbonylamino, under preferred condensation reaction conditions as described under process a) above. From the resulting compound, a compound of formula IV wherein the N-terminal amino group is present in protected form, then the N-terminal protecting group is removed, e.g. in the case of tert-butoxycarbonylamino with hydrogen chloride in dioxane.

Pharmaceutical Preparations and Uses:

The invention relates in particular to a method of treating warm-blooded animals, especially humans, suffering from a disease mentioned above, especially a proliferative disease, especially a tumor disease and in particular such a disease which responds to inhibition of the multicatalytic proteasome complex, which method comprises administering, to warm-blooded animals requiring such treatment, an amount of a compound of formula I that is effective in inhibiting tumors, to the use of a compound of formula I for such treatment, or to the use of a compound of formula I for the preparation of a pharmaceutical composition for such treatment. The invention relates also to the use of a compound of formula I in the inhibition of the multicatalytic proteasome complex in warm-blooded animals, in particular humans.

Effective doses, for example daily doses of approximately 0.05 g to about 10 g, preferably about 0.1 g to about 5 g, for example about 0.15 g to 1.5 g, of a compound of formula I are administered to a warm-blooded animal of approximately 70 kg body weight according to species, age, individual condition, mode of administration and the individual syndrome.

The invention relates also to pharmaceutical compositions comprising a compound of the formula I or a pharmaceutically acceptable salt thereof (active ingredient), especially an effective amount, most especially an amount effective in the prevention or therapy of one of the above-mentioned diseases, of the active ingredient together with pharmaceutically acceptable carriers that are suitable for topical, enteral, for example oral or rectal, or parenteral administration, and may be inorganic or organic, solid or liquid, or any combination thereof. For oral administration there are used especially tablets or gelatin capsules comprising the active ingredient together with diluents, for example lactose, dextrose, sucrose, mannitol, sorbitol, cellulose and/or glycerol, and/or lubricants, for example silicic acid, talc, stearic acid or salts thereof, such as magnesium or calcium stearate, and/or polyethylene glycol. Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. The pharmacologically active compounds of the present invention can also be used in the form of parenterally administrable compositions or in the form of infusion solutions. Such solutions are preferably isotonic aqueous solutions or suspensions, which, for example in the case of lyophilised compositions that comprise the active ingredient alone or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions which, if desired, may comprise further pharmacologically active substances, such as antibiotics, are prepared in a manner known per se, for example by means of conventional mixing, granulating, confectioning, dissolving or lyophilising processes. The concentrations of active ingredient(s) will, of course, vary depending e.g. on the compound of formula I employed, the treatment desired and the nature of the form. The present pharmaceutical compositions comprise approximately from 1% to 100%, especially from approximately 1% to approximately 20%, active ingredient(s).

Compositions for oral administration can for example be obtained by formulating a compound of formula I with a carrier medium comprising a hydrophilic phase, a lipophilic phase and a surfactant. Preferably the composition is in the form of a "microemulsion preconcentrate" or "emulsion preconcentrate", in particular of the type providing o/w (oil-in-water) microemulsions or emulsions. However, the composition may be in the form of a microemulsion or an emulsion which additionally contains an aqueous phase, preferably water. A "microemulsion preconcentrate" is a formulation which spontaneously forms a microemulsion in an aqueous medium, for example in water or in the gastric juices after oral application. A microemulsion is a non-opaque or substantially non-opaque colloidal dispersion that is formed spontaneously or substantially spontaneously when its components are brought into contact. A microemulsion is thermodynamically stable. An "emulsion preconcentrate" is a formulation which spontaneously forms an emulsion in an aqueous medium, for example in water or in the gastric juices, after oral application. The emulsion formed is opaque and thermodynamically stable. The lipophilic phase may comprise about 10 to 85% by weight of the carrier medium; the surfactant may comprise about 5 to 80% by weight of the carrier medium; and the hydrophilic phase may comprise about 10 to 50% by weight of the carrier medium.

The hydrophilic phase may be selected from e.g. Transcutol® ($C_2H_5$—[O—$(CH_2)_2$]$_2$—OH), Glycofurol® (also known as tetrahydrofurfuryl alcohol polyethylene glycol ether) and 1,2-propylene glycol, or mixtures thereof, and is preferably 1,2-propylene glycol. It may include further hydrophilic co-components, for example $C_1$–$C_5$ alkanols.

Preferred lipophilic phase components are medium chain fatty acid triglycerides, mixed mono-, di-, tri-glycerides, and transesterified ethoxylated vegetable oils.

Examples of suitable surfactants are:
i) reaction products of a natural or hydrogenated castor oil and ethylene oxide. The oils available under the trade name Cremophor® (BASF AG, Germany) are especially suitable. Particularly suitable are Cremophor RH 40® (resulting from a 1:40 to 1:45 ratio of hydrogenated castor oil to ethylene oxide during synthesis) and Cremophor RH 60® (resulting from a 1:60 ratio of hydrogenated castor oil to ethylene oxide during synthesis). Also suitable are polyethyleneglycol castor oils such as that available under the trade name Cremophor EL® (resulting from a 1:35 to 1:40 ratio of castor oil to ethylene oxide during synthesis). Similar or identical products which may also be used are available under the trade names Nikkol®, Mapeg®, Incrocas® (Croda Inc., USA) and Tagat® (Th. Goldschmidt, Germany);

ii) polyoxyethylene-sorbitan-fatty acid esters, for example esters of the type known and commercially available under the trade name Tween® (ICI Americas, Inc., USA);

iii) polyoxyethylene fatty acid esters, for example polyoxyethylene stearic acid esters of the type known and commercially available under the trade name Myrj® (ICI Americas, Inc., USA).

iv) polyoxyethylene-polyoxypropylene co-polymers and block co-polymers, e.g. of the type known and commercially available under the trade names Pluronic® (BASF AG, Germany), Emkalyx® and Poloxamer®, especially preferred are Pluronic F68® and Poloxamer 188®;

v) Dioctylsulfosuccinate or di-[2-ethylhexyl]-succinate.

vi) Phospholipids, in particular lecithins.

vii) Propylene glycol mono- and di-fatty acid esters.

The surfactant selected preferably has an HLB (hydrophilic/ipophilic balance) of at least 10. Full physical characteristics of the products referred to herein by trade name can be obtained e.g. from H. P. Fiedler, "Lexikon der Hilfsstoffe für Pharmazie, Kosmetik und Angrenzende Gebiete", Editio Cantor, D-7960 Aulendorf, Germany, 3rd revised and expanded edition (1989).

For example, a suitable pharmaceutical preparation is formulated from a Cremophor®/ethanol 2:1 mixture which, for i.v. injection purposes, is diluted 1:4 (v/v) with a 5% dextrose solution in water.

The pharmaceutical compositions may also include further additives or ingredients, for example antioxidants. They exhibit especially advantageous properties when administered orally, for example in terms of consistency and high level of bioavailability obtained in standard bioavailability trials. Pharmacokinetic parameters, for example absorption and blood levels, also become surprisingly more predictable and problems in administration with erratic absorption may be eliminate or reduced. Additionally, the pharmaceutical composition is effective with tenside materials, for example bile salts, present in the gastro-intestinal tract.

The pharmaceutical compositions for oral use are preferably compounded in unit dosage form, for example by filling them into orally administrable capsule shells. The capsule shells may be soft or hard gelatine capsule shells. However, if desired the pharmaceutical compositions may be in a drink solution form and may include water or any other aqueous system, to provide emulsion or microemulsion systems suitable for drinking.

The present invention relates in particular to the use of compounds of formula I in the manufacture of a pharmaceutical composition for the treatment of a proliferative disease, e.g. of a solid tumor, and their use for the treatment of such a proliferative disease.

EXAMPLES

The following Examples illustrate the invention but do not limit the scope thereof in any way.

| Abbreviations: | |
|---|---|
| abs. | absolute |
| i-BuB(OH)$_2$ | Isobutyl-boronic acid |
| DIEA | N-Ethyldiisopropylamine |
| DMF | N,N-Dimethyl-formamide |
| equiv | equivalent(s) |
| ES-MS | Electrospray Mass Spectroscopy |
| EtOAc | ethyl acetate |
| h | hour(s) |
| HPLC | High Performance Liquid Chromatography |
| MeOH | methanol |
| min | minute(s) |
| m.p. | melting point |
| MPLC | Medium Pressure Liquid Chromatography |
| R$_f$ | ratio of fronts value obtained by TLC on silica gel 60 F254 (Merck, Darmstadt) |
| rt | room temperature |
| TBTU | O-(Benzotriazol-1-yl)-N,N,N',N'-tetramethyluronium tetrafluoroborate |
| TFA | trifluoroacetic acid |
| TLC | Thin Layer Chromatography |
| t$_R$ | retention time |

Ratios of eluents and other solvent mixtures are given in volume by volume (v/v), if not mentioned otherwise.

Visualization of TLC:

TLC spots of final compounds or interemediates that are not detectable by UV-irradiation are visualized using a potassium permanganate staining solution followed by heating the plate.

Composition of potassium permanganate staining solution:

2.5 g of KMnO$_4$ (Potassium permanganate) (Fluka, Buchs, Switzerland)

in 800 ml of H$_2$O and 200 ml of 1N H$_2$SO$_4$

Analytical HPLC Conditions:

System 1

Linear gradient 2–100% CH$_3$CN (0.1% TFA) and H$_2$O (0.1% TFA) in 10 min+2 min 100% CH$_3$CN (0.1% TFA); detection at 215 nm, flow rate 0.7 mL/min at 25° C. Column: Nucleosil 120-3 C18 (125×3.0 mm).

System 2

Linear gradient 20–100% CH$_3$CN (0.1% TFA) and H$_2$O (0.1% TFA) in 7 min+2 min 100% CH$_3$CN (0.1% TFA); detection at 215 nm, flow rate 1 mL/min at 30° C. Column: Nucleosil 100-3 C18HD (125×4 mm).

System 3

Linear gradient 20–100% CH$_3$CN (0.1% TFA) and H$_2$O (0.1% TFA) in 7 min+2 min 100% CH$_3$CN (0.1% TFA); detection at 215 nm, flow rate 1 mL/min at 30° C. Column: Nucleosil 100-3 C8 HD (125×4 mm).

Synthetic Scheme 1 (Examples 1 and 2):

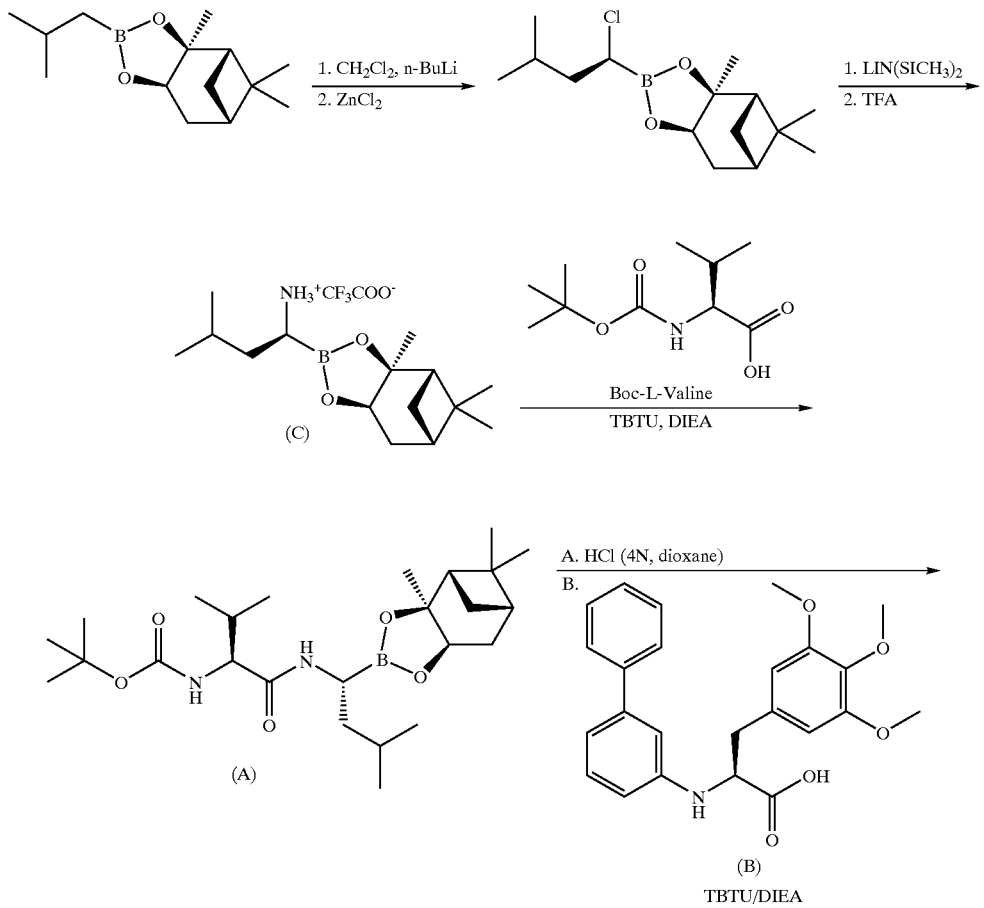

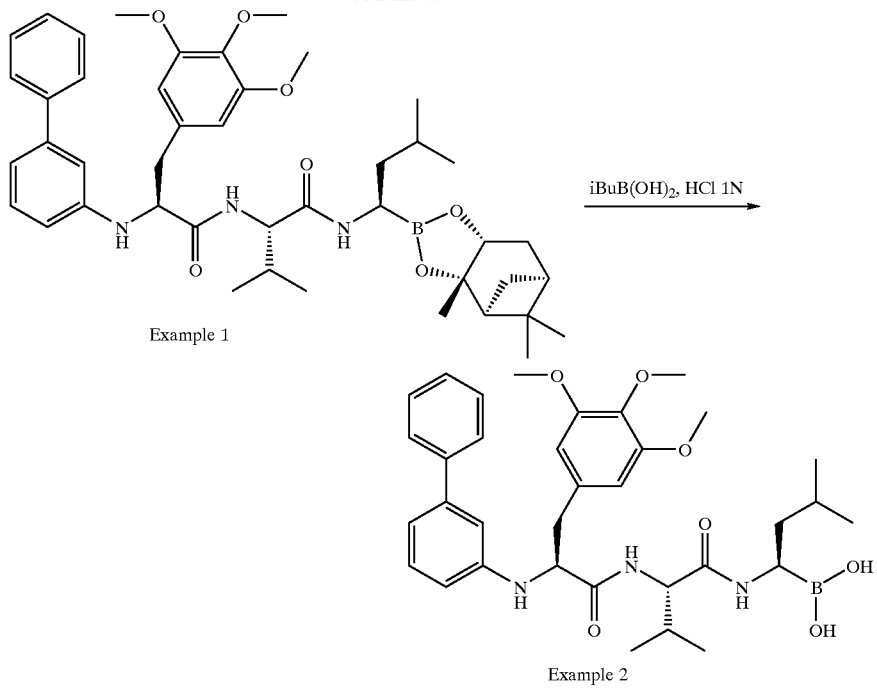

Example 1

Example 2

Example 1

(S)-2-[(S)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide Step A: A 4N solution of HCl in dioxane (5.7 mL, 22.77 mMol, 30 equiv) is added to a cold (0° C.) solution of {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl-]propyl}-carbamic acid tert-butyl ester ((A) in Synthetic Scheme 1) (0.352 g, 0.759 mMol) in CH$_2$Cl$_2$ abs. (5.5 mL), under an argon atmosphere. The resulting mixture is allowed to warm to rt and stirred for 10 min. Additional 4N HCl (1.9 mL, 7.59 mMol, 10 equiv) is added. The reaction mixture is stirred for 10 min and concentrated to afford the crude hydrochloride as a yellow foam.

Step B: DIEA abs. (0.72 mL, 4.14 mMol, 5 equiv) is added dropwise (1.9 mL/min) to a cold (0° C.) solution of the crude hydrochloride (0.331 g, 0.828 mMol), (S)-2-(Biphenyl-3-ylamino)-3-(3,4,5-trimethoxy-phenyl)-propionic acid ((B) in Synthetic Scheme 1) (0.518 g, 0.994 mMol, 1.2 equiv), and TBTU (0.292 g, 0.910 mMol, 1.1 equiv) in DMF abs. (3.0 mL), under an argon atmosphere. The reaction mixture is allowed to warm to rt, stirred for 40 min and poured onto 0° C. H$_2$O (45 mL). The resulting precipitate is collected by vacuum filtration, dissolved in EtOAc and washed with H$_2$O. The organic phase is dried (Na$_2$SO$_4$), filtered and concentrated. The residue is purified by silica gel (25 g) column chromatography (CH$_2$Cl$_2$/MeOH, 90/10) to afford the title compound as a yellow foam.

Title compound: ES-MS: 754.2 [M+H]$^+$; HPLC: single peak at t$_R$=11.85 min (System 1); R$_f$=0.72 (CH$_2$Cl$_2$/MeOH, 90/10).

The starting materials are prepared as follows:

(a) (S)-2-(Biphenyl-3-ylamino)-3-(3,4,5-trimethoxy-phenyl)-propionic acid (for Step B)

The title compound is prepared by heating a suspension of 3-bromo-biphenyl (1.47 mL, 8.54 mMol, Aldrich 25,538-6), (S)-2-amino-3-(3,4,5-trimethoxy-phenyl)-propionic acid (3,4,5-OCH$_3$-phe-OH) (3.27 g, 12.81 mMol), K$_2$CO$_3$ (1.189, 8.54 mMol) and CuI (163 mg, 0.854 mMol) in DMF abs. (10.6 mL) for 24 h at 90° C., under an argon atmosphere. The resulting mixture is allowed to cool to rt, then concentrated in vacuo and purified by MPLC (CH$_3$CN/H$_2$O/TFA) to afford the title compound.

Title compound: ES-MS: 408.2 [M+H]$^+$; HPLC: single peak at t$_R$=8.86 min (System 1).

(b) (S)-2-Amino-3-(3,4,5-trimethoxy-phenyl)-propionic acid (L-3,4,5-Trimethoxy-phenylalanine)

The title compound is preprared from commercially available 3,4,5-trimethoxybenzaldehyde and N-acetylglycine according to a literature procedure (E. M. Oltz, R. C. Bruening, M. J. Smith, K. Kustin and K. Nakanishi in *J. Am. Chem.* 1998, 110 (18), 6162–6172). The resolution of the racemic N-acetyl-3,4,5-trimethoxy-phenylalanine methyl ester is performed by enzyme-catalyzed hydrolysis of the L-ester using Alcalase® (Novo Nordisk) as described in the literature (J. J. Nestor, Jr., T. L. Ho, R. A. Simpson, B. L. Horner, G. H. Jones, G. I. McRae and B. H. Vickery in *J. Med. Chem.* 1982, 25 (7), 795–801; or O. D. Tyagi & P. M. Boll in *Indian J. Chem.* 1992, pp. 851–854).

Title compound: [α]$_D^{20}$=18.9° (c=1.025, H$_2$O); ES-MS: 256.1 [M+H]$^+$; HPLC: single peak at t$_R$=2.08 min (System 2).

(c) {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester The title compound is prepared as described in step B of example 1 but using (S)-3-Methyl-1-((1S,2S,6R,8S)-2,9,9-trimethyl-3,5-dioxa-4-bora-tricyclo[6.1.1.0$^{2,6}$]dec-4-yl)-butylammonium trifluoroacetate ((C) in Synthetic Scheme 1) (for preparation see Kettner, C. A. and Shenvi, A. B. *J. Biol. Chem.* 1984, 259, p. 15106–15114 and Matteson, D. S. and Sadhu, K. M. *J. Am. Chem. Soc.* 1981, 103, p. 5241–5242) (2.395 g, 6.32 mMol), Boc-L-valine (1.373 g, 6.32 mMol), TBTU (2.23 g, 6.95 mMol, 1.1 equiv), DIEA (3.3 mL, 18.95 mMol, 3.0 equiv) and DMF (24 mL).

Title compound: ES-MS: 465.1 [M+H]$^+$; HPLC: single peak at $t_R$=9.95 min (System 1).

Example 2

(R)-1-{(S)-2-[(S)-2-(Biphenyl-3-ylamino)-3-(3,4,5-trimethoxy-phenyl)-propionylamino]-3-methyl-butyrylamino}-3-methyl-butylboronic acid I-BuB(OH)$_2$ is added to a mixture of (S)-2-[(S)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, methanol (4.3 mL), hexane (4.3 mL) and 1N HCl (1.45 mL). The reaction mixture is stirred for 2 h at rt and then diluted with methanol (8 mL) and hexane (8 mL). The two layers are separated. The methanol layer is washed twice with hexane, diluted with CH$_2$Cl$_2$, washed with H$_2$O, dried (Na$_2$SO$_4$), filtered and concentrated. The residue is dissolved in CH$_2$Cl$_2$ and purified by silica gel (20 g) column chromatography (CH$_2$Cl$_2$/MeOH, 80/20) to afford the title compound as a pale yellow foam.

Title compound: ES-MS: 618.2 [M−H]$^−$; $R_f$=0.03 (CH$_2$Cl$_2$/MeOH, 95/5).

Synthetic Scheme 2 (Examples 3 and 4):

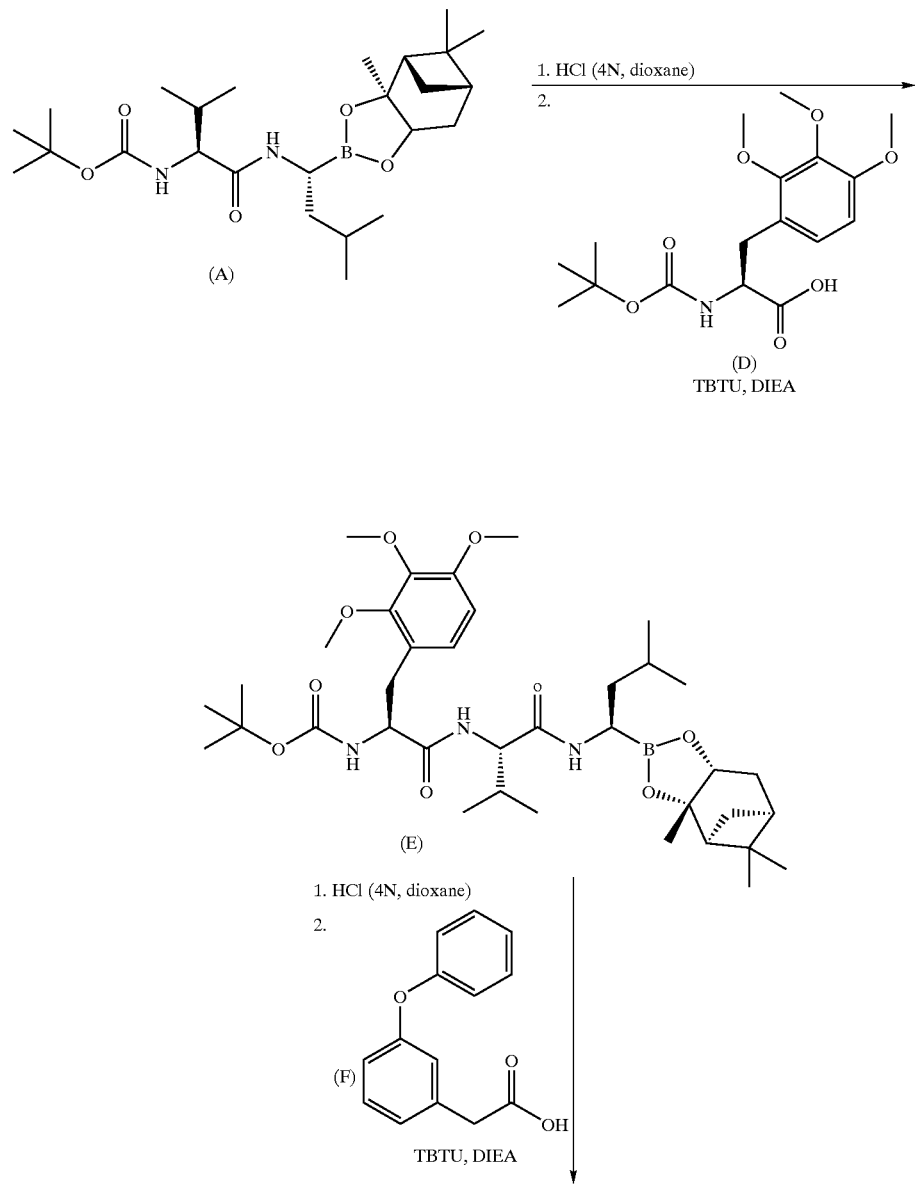

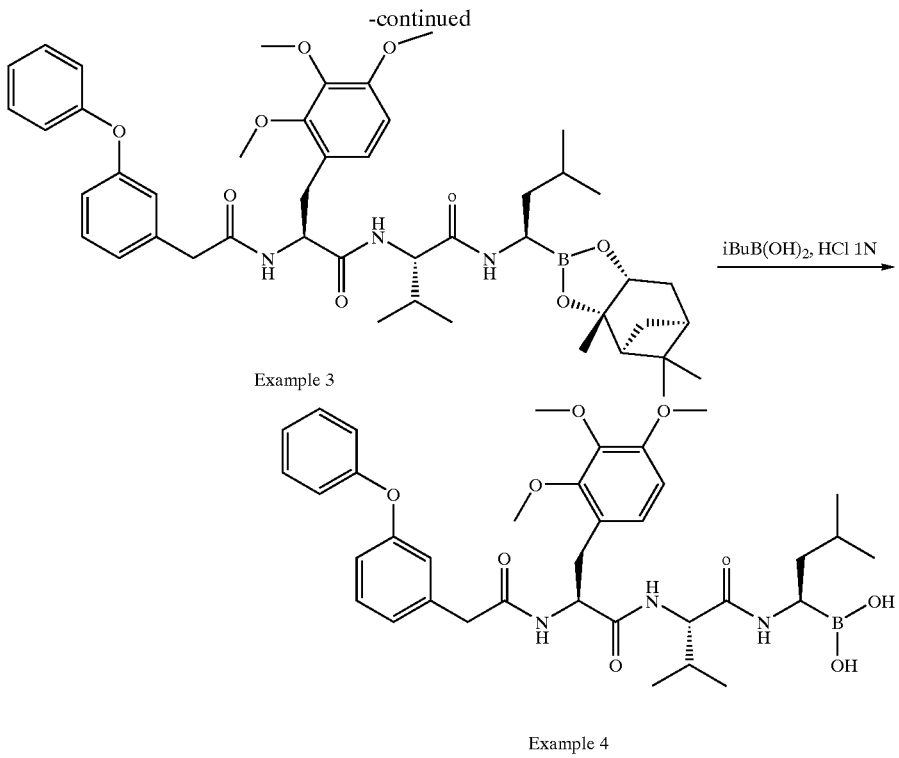

Example 3

Example 4

Example 3

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-[2-(3-phenoxy-phenyl)-acetylamino]-3-(2,3,4-trimethoxy-phenyl)-propionylamino]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester ((A) in Synthetic Scheme 2) by reiteration of the 2-step (deprotection/coupling) procedure described in example 1 but using (S)-2-tert-Butoxycarbonylamino-3-(2,3,4-trimethoxy-phenyl)-propionic acid ((D) in Synthetic Scheme 2) and (3-Phenoxy-phenyl)-acetic acid ((F) in Synthetic Scheme 2) (Trans World Chemicals, Inc.; Rockville, Md., USA) as the partners in each coupling reaction (step B, example 1), respectively. The title compound is obtained as a white solid.

Title compound: ES-MS: 812.1 [M+H]$^+$; HPLC: single peak at $t_R$=11.13 min (System 1); $R_f$=0.41 (CH$_2$Cl$_2$/MeOH, 95/5).

Step 3.1: (S)-2-Amino-3-(2,3,4-trimethoxy-phenyl)-propionic acid (L-2,3,4-Trimethoxyphenyl-alanine)

The title compound is prepared as described for (S)-2-Amino-3-(3,4,5-trimethoxy-phenyl)-propionic acid (example 1).

Title compound: ES-MS: 256.1 [M+H]$^+$; HPLC: $t_R$=2.54 min (System 2); [α]$_D^{20}$=18.5° (c=0.99, H$_2$O).

Step 3.2: (S)-2-tert-Butoxycarbonylamino-3-(2,3,4-trimethoxy-phenyl)-propionic acid The title compound is synthesised starting from (S)-2-Amino-3-(2,3,4-trimethoxy-phenyl)-propionic acid according to a procedure known in the art (M. Bodanszky in Principles of Peptide Synthesis, Akad.-Verlag, 1984).

Title compound: ES-MS: 356.1 [M+H]$^+$; HPLC: $t_R$=5.35 min (System 1); [α]$_D^{20}$=2.0° (c=0.985, MeOH).

Example 4

(R)-3-Methyl-1-{(S)-3-methyl-2-[(S2-[2-(3-phenoxy-phenyl)-acetylamino]-3-(2,3,4-trimethoxy-phenyl)-propionylamino]-butyrylamino}-butylboronic acid The title compound is prepared as described in example 2; ES-MS: 676.0 [M−H]$^−$; $R_f$=0.025 (CH$_2$Cl$_2$/MeOH, 95/5).

Example 5

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-(3-phenyl-propionyl-amino)-3-(2,3,4-trimethoxyphenyl)-propionylamino]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using (S)-2-(tert-butyloxycarbonyl-amino)-3-(2,3,4-trimethoxy-phenyl)-propionic acid and 3-Phenyl-propionic acid (Fluka, Buchs, Switzerland) as the partners in each coupling reaction (step B, example 1), respectively.

Title compound: ES-MS: 734.1 [M+H]$^+$; HPLC: single peak at $t_R$=11.25 min (System 1); $R_f$=0.41 (CH$_2$Cl$_2$/MeOH, 95/5).

Example 6

(R)-3-Methyl-1-{(S)-3-methyl-2-[(S)-2-(3-phenyl-propionylamino)-3-(2,3,4-trimethoxy-phenyl)-propionylamino]-butyrylamino}-butylboronic acid The title compound is prepared as described in example 2; ES-MS: 598.2 [M−H]$^−$; $R_f$=0.025 (CH$_2$Cl$_2$/MeOH, 95/5).

Example 7

(S)-2-[(S)-2-(Biphenyl-3-ylamino)-3-(4-methoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(Biphenyl-3-ylamino)-3-(4-methoxy-phenyl)-propionic acid.

Title compound: ES-MS: 694.4 [M+H]$^+$; HPLC: single peak at $t_R$=12.01 min (System 1); $R_f$=0.56 (CH$_2$Cl$_2$/MeOH, 95/5).

Step 7.1: (S)-2-(Biphenyl-3-ylamino)-3-(4-methoxy-phenyl)-propionic acid

The title compound is prepared as described for (S)-2-(Biphenyl-3-ylamino)-3-(3,4,5-trimethoxy-phenyl)-propionic acid (example 1) but using O-methyl-L-tyrosine (Bachem).

Purification by MPLC (CH$_3$CN/H$_2$O/TFA) afforded the title compound; ES-MS: 348.3 [M+H]$^+$; HPLC: single peak at $t_R$=9.52 min (System 1).

Example 8

(R)-1-{(S)-2-[(S)-2-(Biphenyl-3-ylamino)-3-(4-methoxy-phenyl)-propionylamino]-3-methyl-butyrylamino}-3-methyl-butylboronic acid The title compound is prepared as described in example 2; ES-MS: 558.0 [M−H]$^−$; HPLC: $t_R$=6.47 min (System 3); $R_f$=0.086 (CH$_2$Cl$_2$/MeOH, 95/5).

Example 9

(S)-2-[(S)-2-(Biphenyl-3-ylamino)-3-(3,4-dimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(Biphenyl-3-ylamino)-3-(3,4-dimethoxy-phenyl)-propionic acid.

Title compound: ES-MS: 724.4 [M+H]$^+$; HPLC: single peak at $t_R$=11.75 min (System 1); $R_f$=0.41 (CH$_2$Cl$_2$/MeOH, 95/5).

Step 9.1: (S)-2-(Biphenyl-3-ylamino)-3-(3,4-dimethoxy-phenyl)-propionic acid

The title compound is prepared as described for (S)-2-(Biphenyl-3-ylamino)-3-(3,4,5-trimethoxy-phenyl)-propionic acid (example 1) but using 3-(3,4-dimethoxyphenyl)-L-alanine (Aldrich). Purification by MPLC (CH$_3$CN/H$_2$O/TFA) afforded the title compound; ES-MS: 378.2 [M+H]$^+$; HPLC: single peak at $t_R$=9.10 min (System 1).

Example 10

(R)-1-{(S)-2-[(S)-2-(Biphenyl-3-ylamino)-3-(3,4-dimethoxy-phenyl)-propionylamino]-3-methyl-butyrylamino}-3-methyl-butylboronic acid The title compound is prepared as described in example 2; ES-MS: 588.2 [M−H]$^−$; $R_f$=0.090 (CH$_2$Cl$_2$/MeOH, 95/5).

Example 11

(S)-2-[(S)-2-(3-Isopropyl-phenylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(3-Isopropyl-phenylamino)-3-(3,4,5-trimethoxy-phenyl)-propionic acid.

Title compound: ES-MS: 720.4 [M+H]$^+$; HPLC: single peak at $t_R$=11.85 min (System 1); $R_f$=0.43 (CH$_2$Cl$_2$/MeOH, 95/5).

Step 11.1: (S)-2-(3-Isopropyl-phenylamino)-3-(3,4,5-trimethoxy-phenyl)-propionic acid The title compound is prepared as described for (S)-2-(Biphenyl-3-ylamino)-3-(3,4,5-trimethoxy-phenyl)-propionic acid (example 1) but using 1-bromo-3-isopropylbenzene (Lancaster). Purification by MPLC (CH$_3$CN/H$_2$O/TFA) afforded the title compound; ES-MS: 374.1 [M+H]$^+$; HPLC: single peak at $t_R$=8.95 min (System 1).

Example 12

(R)-1-{(S)-2-[(S)-2-(3-Isopropyl-phenylamino)-3-(3,4,5-trimethoxy-phenyl)-propionylamino]-3-methyl-butyrylamino}-3-methyl-butylboronic acid The title compound is prepared as described in example 2; ES-MS: 584.3 [M−H]$^−$; $R_f$=0.13 (CH$_2$Cl$_2$/MeOH, 95/5).

Example 13

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-(3-pyridin-2-yl-phenylamino)-3-(3,4,5-trimethoxy-phenyl)-propionylamino]-butyramide The title compound is prepared as described in example 1 but using (S)-2-(3-Pyridin-2-yl-phenylamino)-3-(3,4,5-trimethoxy-phenyl)-propionic acid.

Title compound: ES-MS: 755.3 [M+H]$^+$; HPLC: single peak at $t_R$=9.97 min (System 1); $R_f$=0.23 (CH$_2$Cl$_2$/MeOH, 95/5).

Step 13.1: 2-(3-Bromo-phenyl)-pyridine

The title compound is prepared according to literature procedures: Zhang, Biliang, Breslow, Ronald Ester Hydrolysis by a Catalytic Cyclodexttin Dimer Enzyme Mimic with a Metallobipyridyl Linking Group. J. Am. Chem. Soc. (1997), 119(7), 1676–1681; M. Van der Sluis, V. Beverwijk, A. Termaten, F. Bickelhaupt, H. Kooijman, A. L. Spek Synthesis of Novel Phosphaalkene-Based Bidentate Ligands Mes*P:CH (3-R—Ar) (R=Pyridyl, Carbaldimino) and Formation of Three-Membered Palladacycles Mes*(Me)P—CH (3-R—Ar)—PdCl by Carbopalladation of the P:C Double Bond. Organometallics (1999), 18(8), 1402–1407.

Title compound: ES-MS: 235.0 [M+H]$^+$; HPLC: single peak at $t_R$=6.64 min (System 1); $R_f$=0.17 (Hexane/Et$_2$O, 80/20).

Step 13.2: (S)-2-(3-Pyridin-2-yl-phenylamino)-3-(3,4,5-trimethoxy-phenyl)-propionic acid The title compound is prepared as described for (S)-2-(Biphenyl-3-ylamino)-3-(3,4,5-trimethoxy-phenyl)-propionic acid (example 1) but using 2-(3-Bromo-phenyl)-pyridine. Purification by MPLC (CH$_3$CN/H$_2$O/TFA) afforded the title compound; ES-MS: 409.2 [M+H]$^+$; HPLC: single peak at $t_R$=6.64 min (System 1).

Example 14

(R)-3-Methyl-1-[(S)-3-methyl-2-[(S)-2-(3-pyridin-2-yl-phenylamino)-3-(3,4,5-trimethoxy-phenyl)-propionylamino]-butyrylamino)-butylboronic acid The title compound is prepared as described in example 2; ES-MS: 619.2 [M−H]$^−$; $R_f$=0.044 (CH$_2$Cl$_2$/MeOH, 95/5).

Example 15

(S)-2-[(S)-2-(Biphenyl-3-ylamino)-3-(2,3,4-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(Biphenyl-3-ylamino)-3-(2,3,4-trimethoxy-phenyl)-propionic acid.

Title compound: ES-MS: 754.4 [M+H]$^+$; HPLC: single peak at $t_R$=12.08 min (System 1); $R_f$=0.66 (CH$_2$Cl$_2$/MeOH, 95/5).

Step 15.1: (S)-2-(Biphenyl-3-ylamino)-3-(2,3,4-trimethoxy-phenyl)-propionic acid The title compound is prepared as described for (S)-2-(Biphenyl-3-ylamino)-3-(3,4,5-trimethoxy-phenyl)-propionic acid (example 1) but using (S)-2-Amino-3-(2,3,4-trimethoxy-phenyl)-propionic acid. Purification by MPLC (CH$_3$CN/H$_2$O/TFA) afforded the title compound; ES-MS: 408.2 [M+H]$^+$; HPLC: single peak at $t_R$=9.42 min (System 1).

Example 16

(R)-1-{(S)-2-[(S)-2-(Biphenyl-3-ylamino)-3-(2,3,4-trimethoxy-phenyl)-propionylamino]-3-methyl-butyrylamino}-3-methyl-butylboronic acid The title compound is prepared as described in example 2; ES-MS: 618.3 [M−H]$^−$; $R_f$=0.23 (CH$_2$Cl$_2$/MeOH, 95/5).

Example 17

(S)-2-[(S)-3-(4-Benzyloxy-phenyl)-2-(biphenyl-3-ylamino)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-3-(4-Benzyloxyphenyl)-2-(biphenyl-3-ylamino)-propionic acid.

Title compound: ES-MS: 770.3 [M+H]$^+$; HPLC: single peak at $t_R$=12.45 min (System 1); $R_f$=0.74 (CH$_2$Cl$_2$/MeOH, 95/5).

Step 17.1: (S)-3-(4-Benzyloxy-phenyl)-2-(biphenyl-3-ylamino)-propionic acid

The title compound is prepared as described for (S)-2-(Biphenyl-3-ylamino)-3-(3,4,5-trimethoxy-phenyl)-propionic acid (example 1) but using (S)-2-Amino-3-(4-benzyloxy-phenyl)-propionic acid (O-benzyl-L-tyrosine). Purification by MPLC (CH$_3$CN/H$_2$O/TFA) afforded the title compound; ES-MS: 424.3 [M+H]$^+$; HPLC: single peak at $t_R$=10.40 min (System 1).

Example 18

(R)-1-{(S)-2-[(S)-3-(4-Benzyloxy-phenyl)-2-(biphenyl-3-ylamino)-propionylamino]-3-methyl-butyrylamino}-3-methyl-butylboronic acid The title compound is prepared as described in example 2; ES-MS: 633.9 [M−H]$^−$; $R_f$=0.65 (CH$_2$Cl$_2$/MeOH, 90/10).

Example 19

(R)-2-[(S)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo-[6.1.1.0$^{2,6}$]dec-4-yl)-butyl]-butyramide The title compound is prepared as described in example 1 but using {(R)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester.

Title compound: ES-MS: 754.1 [M+H]$^+$; HPLC: single peak at $t_R$=11.73 min (System 1); $R_f$=0.52 (CH$_2$Cl$_2$/MeOH, 95/5).

Step 19.1: {(R)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester The title compound is prepared as described for {(S)-2-Methyl-1-[(R)-3-methyl-1-((1S,2S,6R,8S)-2,9,9-trimethyl-3,5-dioxa-4-bora-tricyclo[6.1.1.0$^{2,6}$]-dec-4-yl)-butylcarbamoyl]-propyl}-carbamic acid tert-butyl ester (example 1 (c)) but using Boc-D-valine (Fluka).

Title compound: ES-MS: 465.4 [M+H]$^+$.

Example 20

(R)-1-{(R)-2-[(S)-2-(Biphenyl-3-ylamino)-3-(3,4,5-trimethoxy-phenyl)-propionylamino]-3-methyl-butyrylamino}-3-methyl-butylboronic acid The title compound is prepared as described in example 2; ES-MS: 618.2 [M−H]$^−$; $R_f$=0.088 (CH$_2$Cl$_2$/MeOH, 95/5).

Example 21

(S)-2-[(R)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^2$]dec-4-yl)-butyl]-butyramide The title compound is prepared as described in example 1 but using (R)-2-(Biphenyl-3-ylamino)-3-(3,4,5-trimethoxy-phenyl)-propionic acid.

Title compound: ES-MS: 754.3 [M+H]$^+$; HPLC: single peak at $t_R$=11.71 min (System 1); $R_f$=0.67 (CH$_2$Cl$_2$/MeOH, 95/5).

Step 21.1: (R)-2-(Biphenyl-3-ylamino)-3-(3,4,5-trimethoxy-phenyl)-propionic acid The title compound is prepared as described for (S)-2-(Biphenyl-3-ylamino)-3-(3,4,5-trimethoxy-phenyl)-propionic acid (example 1) but using (R)-2-amino-3-(3,4,5-trimethoxyphenyl)-propionic acid (3,4,5-OCH$_3$-phe-OH).

Title compound: ES-MS: 408.2 [M+H]$^+$; HPLC: single peak at $t_R$=9.10 min (System 1).

For the synthesis of (R)-2-amino-3-(3,4,5-trimethoxyphenyl)-propionic acid see example 1. After the enzymatic resolution, the remaining D-aminoacid-methylester is hydrolysed and deacetylated using protocols known in the art; [α]$_D^{20}$=+19.7° (c=1.04, H$_2$O); ES-MS: 256.2 [M+H]$^+$; single peak at $t_R$=2.11 min (System 2).

Example 22

(R)-1-{(S)-2-[(R)-2-(Biphenyl-3-ylamino)-3-(3,4,5-trimethoxy-phenyl)-propionylamino]-3-methyl-butyrylamino}-3-methyl-butylboronic acid The title compound is prepared as described in example 2; ES-MS: 618.2 [M−H]$^−$; $R_f$=0.20 (CH$_2$Cl$_2$/MeOH, 90/10).

Example 23

(S)-2-[(S)-2-(Biphenyl-3-ylamino)-3-(3,4,5-trimethoxy-phenyl)-propionylamino]-3-methyl-N-[3-methyl-1-(4,4,5,5-tetramethyl-[1,3,2]dioxaborolan-2-yl)-butyl]-butyramide The title compound is prepared as described in example 1 but using {(S)-2-Methyl-1-[3-methyl-1-(4,4,5,5- tetramethyl-[1,3,2]dioxaborolan-2-yl)-butylcarbamoyl]-propyl}-carbamic acid tert-butyl ester.

The title compound is obtained as a crude product; ES-MS: 702.3 [M+H]$^+$; HPLC: $t_R$=10.31 min (System 1).

Step 23.1: {(S)-2-Methyl-1-[3-methyl-1-(4,4,5,5-tetramethyl-[1,3,2]dioxaborolan-2-yl)-butylcarbamoyl]-propyl}-carbamic acid tert-butyl ester The title compound is prepared in analogy to the synthesis of {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (example 1 (c)).

Title compound: ES-MS: 413.3 [M+H]$^+$.

Example 24

1-{(S)-2-[(S)-2-(Biphenyl-3-ylamino)-3-(3,4,5-trimethoxy-phenyl)-propionylamino]-3-methyl-butyrylamino}-3-methyl-butylboronic acid The title compound is prepared as described in example 2; ES-MS: 618.2 [M−H]$^−$; R$_f$=0.076 (CH$_2$Cl$_2$/MeOH, 95/5); HPLC: two peaks at $t_R$=6.23 min and 6.36 min (ratio 1:1) (System 3).

Example 25

(S)-2-{(S)-3-(3,4-Dimethoxy-phenyl)-2-[2-(3-phenoxy-phenyl)-acetylamino]-propionylamino}-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using Boc-L-3,4-dimethoxyphenylalanine (Synthetech) and (3-Phenoxyphenyl)-acetic acid (Trans World Chemicals, Inc.; Rockville, Md., USA) as the partners in each coupling reaction (step B, example 1), respectively. The title compound is obtained as a foam; ES-MS: 782.3 [M+H]$^+$; HPLC: single peak at $t_R$=11.76 min (System 1); R$_f$=0.61 (CH$_2$Cl$_2$/MeOH, 90/10).

Example 26

(R)-1-((S)-2-{(S)-3-(3,4-Dimethoxy-phenyl)-2-[2-(3-phenoxy-phenyl)-acetylamino]-propionylamino}-3-methyl-butyrylamino)-3-methyl-butylboronic acid The title compound is prepared as described in example 2; ES-MS: 646.2 [M−H]$^−$; HPLC: single peak at $t_R$=5.90 min (System 3); R$_f$=0.12 (CH$_2$Cl$_2$/MeOH, 90/10).

Example 27

(S)-3-Methyl-N-[(R)-3-methyl-1-((1S,2S,6R,8S)-2,9,9-trimethyl-3,5-dioxa-4-bora-tricyclo[6.1.1.0$^{2,6}$] dec-4-yl)-butyl]-2-[(S)-2-[2-(3-phenoxy-phenyl)-acetylamino]-3-(3,4,5-trimethoxy-phenyl)-propionylamino]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using (S2-tert-Butoxycarbonylamino-3-(3,4, 5-trimethoxy-phenyl)-propionic acid and (3-Phenoxy-phenyl)-acetic acid (Trans World Chemicals, Inc.; Rockville, Md., USA) as the partners in each coupling reaction (step B, example 1), respectively. The title compound is obtained as a yellow foam; ES-MS: 812.4 [M+H]$^+$; HPLC: single peak at $t_R$=11.36 min (System 1); R$_f$=0.53 (CH$_2$Cl$_2$/MeOH, 95/5).

Step 27.1: (S)-2-tert-Butoxycarbonylamino-3-(3,4,5-trimethoxy-phenyl)-propionic acid The title compound is synthesised as described for (S)-2-tert-Butoxycarbonylamino-3-(2,3,4-trimethoxy-phenyl)-propionic acid (Example 3) but starting from (S)2-Amino-3-(3,4,5-trimethoxy-phenyl)-propionic acid.

Title compound: ES-MS: 356 [M+H]$^+$; HPLC: $t_R$=4.83 min (System 2); m.p.=76–80° C.; [α]$_D^{20}$=+13.4° (c=1.01, methanol).

Example 28

(R)-3-Methyl-1-{(S)-3-methyl-2-[(S)-2-[2-(3-phenoxy-phenyl)-acetylamino]-3-(3,4,5-trimethoxy-phenyl)-propionylamino]-butyrylamino}-butylboronic acid The title compound is prepared as described in example 2; ES-MS: 676.2 [M−H]$^−$; R$_f$=0.14 (CH$_2$Cl$_2$/MeOH, 95/5).

Example 29

(S)-2-{(S)-3-(4-Benzyloxy-phenyl)-2-[2-(3-benzyloxy-phenyl)-acetylamino]-propionylamino}-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]-dec-4-yl)-butylcarbamoyl]-propyl}-carbamic acid tert-butyl ester by reiteration of the 2-step (deprotection/coupling) procedure described in example 1 but using (S)-3-(4-Benzyloxy-phenyl)-2-tert-butoxycarbonylamino-propionic acid and (3-Phenoxy-phenyl)-acetic acid (Trans World Chemicals, Inc.; Rockville, Md., USA) as the partners in each coupling reaction (step B, example 1), respectively. The title compound is obtained as a beige foam; ES-MS: 842.0 [M+H]$^+$; HPLC: single peak at $t_R$=12.19 min (System 1); R$_f$=0.37 (CH$_2$Cl$_2$/MeOH, 95/5).

Step 29.1: (S)-3-(4-Benzyloxy-phenyl)-2-tert-butoxycarbonylamino-propionic acid

The title compound is synthesised as described for (S)-2-tert-Butoxycarbonylamino-3-(2,3,4-trimethoxy-phenyl)-propionic acid (Example 3) but starting from O-Benzyl-L-tyrosine (Fluka).

Title compound: ES-MS: 370.1. [M−H]$^−$; HPLC: $t_R$=9.23 min (System 1).

Example 30

(R)-1-((S)-2{(S)-3-(4-Benzyloxy-phenyl)-2-[2-(3-benzyloxy-phenyl)-acetylamino]-propionylamino}-3-methyl-butyrylamino)-3-methyl-butylboronic acid The titled compound is prepared as described in example 2; ES-MS: 705.8 [M−H]$^−$; R$_f$=0.12 (CH$_2$Cl$_2$/MeOH, 95/5).

Example 31

(S)-2-[(S)-2-(Biphenyl-3-ylamino)-3-(3,4,5-trimethoxy-phenyl)-propionylamino]-4-methyl-pentanoic acid [(R)-3-methyl-1-((1S,2S,6R,8S)-2,9, 9-trimethyl-3,5-dioxa-4-bora-tricyclo[6.1.1.0$^{2,6}$]dec-4-yl)-butyl]-amide The title compound is prepared as described in example 1 but using {(S)-3-Methyl-1-[(R)-3-methyl-1-((1S,2S,6R,8S)-

2,9,9-trimethyl-3,5-dioxa-4-bora-tricyclo[6.1.1.0$^{2,6}$]dec-4-yl)-butylcarbamoyl]-butyl}-carbamic acid tert-butyl ester.

Title compound: ES-MS: 768.2 [M+H]$^+$; HPLC: single peak at t$_R$=11.79 min (System 1); R$_f$=0.72 (CH$_2$Cl$_2$/MeOH, 95/5).

Step 31.1: {(S)-3-Methyl-1-[(R)-3-methyl-1-((1S,2S,6R,8S)-2,9,9-trimethyl-3,5-dioxa-4-bora-tricyclo[6.1.1.0$^{2,6}$]-dec-4-yl)-butylcarbamoyl]-butyl}-carbamic acid tert-butyl ester The title compound is prepared as described for {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (example 1 (c)) but using Boc-L-leucine.

Title compound: ES-MS: 479.2 [M+H]$^+$; HPLC: single peak at t$_R$=10.05 min (System 1).

Example 32

(R)-1-{(S)-2-[(S)-2-(Biphenyl-3-ylamino)-3-(3,4,5-trimethoxy-phenyl)-propionylamino]-4-methyl-pentanoylamino}-3-methyl-butylboronic acid The title compound is prepared as described in example 2; ES-MS: 632.2 [M−H]$^-$; R$_f$=0.15 (CH$_2$Cl$_2$/MeOH, 95/5).

Example 33

(S)-2-[(S)-2-(Biphenyl-3-ylamino)-3-(3,4-dimethoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide The title compound is prepared as described in example 1 but using {(S)-3-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-butyl}-carbamic acid tert-butyl ester and (S)-2-(Biphenyl-3-ylamino)-3-(3,4-dimethoxy-phenyl)-propionic acid.

Title compound: ES-MS: 738.3 [M+H]$^+$; HPLC: single peak at t$_R$=11.76 min (System 1); R$_f$=0.59 (CH$_2$Cl$_2$/MeOH, 95/5).

Example 34

(R)-1-{(S)-2-[(S)-2-(Biphenyl-3-ylamino)-3-(3,4,5-trimethoxy-phenyl)-propionylamino]-4-methyl-pentanoylamino}-3-methyl-butylboronic acid The title compound is prepared as described in example 2; ES-MS: 602.2 [M−H]$^-$; R$_f$=0.14 (CH$_2$Cl$_2$/MeOH, 95/5).

Example 35

(S)-2-[(S)-2-(Biphenyl-3-ylamino)-3-(4-methoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide The title compound is prepared as described in example 1 but using {(S)-3-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-butyl}-carbamic acid tert-butyl ester and (S)-2-(Biphenyl-3-ylamino)-3-(4-methoxy-phenyl)-propionic acid.

Title compound: ES-MS: 708.3 [M+H]$^+$; HPLC: single peak at t$_R$=12.03 min (System 1); R$_f$=0.70 (CH$_2$Cl$_2$/MeOH, 95/5).

Example 36

(R)-1-{(S)-2-[(S)-2-(Biphenyl-3-ylamino)-3-(4-methoxy-phenyl)-propionylamino]-4-methyl-pentanoylamino}-3-methyl-butylboronic acid The title compound is prepared as described in example 2; ES-MS: 572.1 [M−H]$^-$; R$_f$=0.25 (CH$_2$Cl$_2$/MeOH, 90/10).

Example 37

(S)-2-(Biphenyl-3-ylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(3,4,5-trimethoxy-phenyl)-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]-dec-4-yl)-butylcarbamoyl]-ethyl}-carbamic acid tert-butyl ester.

Title compound: ES-MS: 726.3 [M+H]$^+$; HPLC: single peak at t$_R$=11.24 min (System 1); R$_f$=0.41 (CH$_2$Cl$_2$/MeOH, 95/5).

Step 37.1: {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester The title compound is prepared as described for {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (step 1.1, example 1) but using Boc-L-alanine (Fluka).

Title compound: ES-MS: 437.4 [M+H]$^+$; HPLC: single peak at t$_R$=10.91 min (System 1).

Example 38

(R)-1-{(S)-2-[(S)-2-(Biphenyl-3-ylamino)-3-(3,4,5-trimethoxy-phenyl)-propionylamino]-propionylamino}-3-methyl-butylboronic acid The title compound is prepared as described in example 2; ES-MS: 590.0 [M−H]$^-$; R$_f$=0.12 (CH$_2$Cl$_2$/MeOH, 95/5).

Example 39

(S)-2-(Biphenyl-3-ylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(2,3,4-trimethoxy-phenyl)-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(Biphenyl-3-ylamino)-3-(2,3,4-trimethoxyphenyl)-propionic acid.

Title compound: ES-MS: 726.3 [M+H]$^+$; HPLC: single peak at t$_R$=11.71 min (System 1); R$_f$=0.45 (CH$_2$Cl$_2$/MeOH, 95/5).

Example 40

(R)-1-{(S)-2-[(S)-2-(Biphenyl-3-ylamino)-3-(2,3,4-trimethoxy-phenyl)-propionylamino]-propionylamino}-3-methyl-butylboronic acid The title compound is prepared as described in example 2; ES-MS: 590.0 [M−H]$^-$; R$_f$=0.033 (CH$_2$Cl$_2$/MeOH, 95/5).

Example 41

(S)-2-(Biphenyl-3-ylamino)-3-(4-methoxy-phenyl)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-propionamide The title compound is prepared as described in example 1 but using {(S)-1-[(R)-3-Methyl-1-((1S,2S,6R,8S)-2,9,9- trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(Biphenyl-3-ylamino)-3-(4-methoxy-phenyl)-propionic acid.

Title compound: ES-MS: 666.3 [M+H]$^+$; HPLC: single peak at t$_R$=11.63 min (System 1); R$_f$=0.46 (CH$_2$Cl$_2$/MeOH, 95/5).

Example 42

(R)-1-{(S)-2-[(S)-2-(Biphenyl-3-ylamino)-3-(4-methoxy-phenyl)-propionylamino]-propionylamino}-3-methyl-butylboronic acid The title compound is prepared as described in example 2; ES-MS: 530.3 [M−H]$^−$; R$_f$=0.051 (CH$_2$Cl$_2$/MeOH, 95/5).

Example 43

(S)-2-(Biphenyl-3-ylamino)-3-(3,4-dimethoxy-phenyl)-N-{(S)-1-[(R)3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(Biphenyl-3-ylamino)-3-(3,4-dimethoxyphenyl)-propionic acid.

Title compound: ES-MS: 696.3 [M+H]$^+$; HPLC: single peak at t$_R$=11.39 min (System 1); R$_f$=0.53 (CH$_2$Cl$_2$/MeOH, 95/5).

Example 44

(R)-1-{(S)-2-[(S)-2-(Biphenyl-3-ylamino)-3-(3,4-dimethoxy-phenyl)-propionylamino]-propionylamino}-3-methyl-butylboronic acid The title compound is prepared as described in example 2; ES-MS: 560.2 [M−H]$^−$; R$_f$=0.023 (CH$_2$Cl$_2$/MeOH, 95/5).

Example 45

(S)-2-(3-Isopropyl-phenylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(3,4,5-trimethoxy-phenyl)-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(3-Isopropyl-phenylamino)-3-(3,4,5-trimethoxyphenyl)-propionic acid.

Title compound: ES-MS: 692.3 [M+H]$^+$; HPLC: single peak at t$_R$=11.49 min (System 1); R$_f$=0.24 (CH$_2$Cl$_2$/MeOH, 95/5).

Example 46

(R)-1-{(S)-2-[(S)-2-(3-Isopropyl-phenylamino)-3-(3,4,5-trimethoxy-phenyl)-propionylamino]-propionylamino}-3-methyl-butylboronic acid The title compound is prepared as described in example 2; ES-MS: 560.2 [M−H]$^−$; R$_f$=0.22 (CH$_2$Cl$_2$/MeOH, 95/5).

Example 47

(S)-N-{(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-2-(3-phenyl-propionylamino)-3-(2,3,4 trimethoxy-phenyl)-propionamide The title compound is prepared from {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester by reiteration of the 2-step (deprotection/coupling) procedure described in example 1 but using (S)-2-Amino-3-(2,3,4-trimethoxy-phenyl)-propionic acid and 3-Phenyl-propionic acid (Fluka) as the partners in each coupling reaction (step B, example 1), respectively.

Title compound: ES-MS: 706.3 [M+H]$^+$; HPLC: single peak at t$_R$=10.81 min (System 1); R$_f$=0.32 (CH$_2$Cl$_2$/MeOH, 95/5).

Example 48

(R)-3-Methyl-1-{(S)-2-[(S)-2-(3-phenyl-propionylamino)-3-(2,3,4-trimethoxyphenyl)-propionylamino]-propionylamino}-butylboronic acid The title compound is prepared as described in example 2; ES-MS: 570.3 [M−H]$^−$; R$_f$=0.22 (CH$_2$Cl$_2$/MeOH, 95/5).

Example 49

(S)-2-[(S)-2-(Biphenyl-3-ylamino)-3-(3,4,5-trimethoxy-phenyl)-propionylamino]-3-methyl-N-[(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-butyramide The title compound is prepared as described in example 1 but using {(S)-2-Methyl-1-[(R)-2-phenyl-1-((1S,2S,6R,8S)-2,9,9-trimethyl-3,5-dioxa-4-bora-tricyclo[6.1.1.0$^{2,6}$]-dec-4-yl)-ethylcarbamoyl]-propyl}-carbamic acid tert-butyl ester.

Title compound: ES-MS: 788.0 [M+H]$^+$; HPLC: single peak at t$_R$=11.66 min (System 1); R$_f$=0.79 (CH$_2$Cl$_2$/MeOH, 95/5).

Step 49.1: {(S)-2-Methyl-1-[(R)-2-phenyl-1-((1S,2S,6R,8S)-2,9,9-trimethyl-3,5-dioxa-4-bora-tricyclo[6.1.1.0$^{2,6}$] dec-4-yl)-ethylcarbamoyl]-propyl}-carbamic acid tert-butyl ester The title compound is prepared in analogy to the synthesis of {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (example 1 (c)).

Title compound: ES-MS: 499.1 [M+H]$^+$; HPLC: single peak at t$_R$=10.78 min (System 1).

Example 50

(R)-1-{(S)-2-[(S)-2-(Biphenyl-3-ylamino)-3-(3,4,5-trimethoxy-phenyl)-propionylamino]-3-methyl-butyrylamino}-2-phenyl-ethylboronic acid The title compound is prepared as described in example 2; ES-MS: 652.2 [M−H]$^−$; R$_f$=0.22 (CH$_2$Cl$_2$/MeOH, 95/5).

Example 51

(S)-2-[(S)-2-(Biphenyl-3-ylamino)-3-(4-methoxy-phenyl)-propionylamino]-3-methyl-N-[(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-butyramide The title compound is prepared as described in example 1 but using {(S)-2-Methyl-1-[(R)-2-phenyl-1-((1S,2S,6R,8S)-2,9,9-trimethyl-3,5-dioxa-4-bora-tricyclo[6.1.1.0$^{2,6}$]dec-4-yl)-ethylcarbamoyl]-propyl}-carbamic acid tert-butyl ester and (S)-2-(Biphenyl-3-ylamino)-3-(4-methoxy-phenyl)-propionic acid.

Example 52

(R)-1-{(S)-2-[(S)-2-(Biphenyl-3-ylamino)-3-(4-methoxy-phenyl)-propionylamino]-3-methyl-butyrylamino}-2-phenyl-ethylboronic acid The title compound is prepared as described in example 2; ES-MS: 591.8 [M−H]−; $R_f$=0.13 (CH$_2$Cl$_2$/MeOH, 95/5).

Example 53

Inhibition of the Chymotrypsin-like Activity of the 20S Proteasome

Exemplary IC$_{50}$ values determined according to the test described above for compounds of formula I are given below (Table 1).

TABLE 1

| Example | IC$_{50}$ [µM] (results of one or two experiments) |
|---|---|
| 1 | 0.0046/0.0024 |
| 2 | 0.0028/0.0021 |
| 3 | 0.0017/0.0014 |
| 4 | 0.0019/0.0015 |
| 5 | 0.0013/0.0006 |
| 6 | 0.0018/0.0019 |
| 7 | 0.0029/0.0032 |
| 8 | 0.0028/0.0045 |
| 9 | 0.0017/0.0022 |
| 10 | 0.0029/0.004 |
| 11 | 0.0039 |
| 12 | 0.0038 |
| 13 | 0.0013 |
| 14 | 0.0017 |
| 15 | 0.0071 |
| 16 | 0.0059 |
| 17 | 0.0093 |
| 18 | 0.0015 |
| 21 | 0.0015 |
| 22 | 0.0017 |
| 23 | 0.0021 |
| 24 | 0.0021 |
| 25 | 0.0008 |
| 26 | 0.001 |
| 27 | 0.0003 |
| 28 | 0.0008 |
| 29 | 0.004 |
| 30 | 0.0059 |
| 31 | 0.0022 |
| 32 | 0.0037 |
| 33 | 0.0026 |
| 34 | 0.0013 |
| 35 | 0.0023 |
| 36 | 0.0023 |
| 37 | 0.0013 |
| 38 | 0.0017 |
| 39 | 0.0019 |
| 40 | 0.0022 |
| 41 | 0.0012 |
| 42 | 0.0019 |
| 43 | 0.0018 |
| 44 | 0.001 |
| 45 | 0.0013 |
| 46 | 0.0019 |
| 47 | 0.0008 |
| 48 | 0.0007 |
| 50 | 0.0023 |
| 51 | 0.0043 |
| 52 | 0.005 |

Example 54

Composition for Oral Application 20.0 g of solution for oral application of any one of the title compounds given in Examples 1 to 6 can be prepared as follows (% means weight ingredient/total weight solution):

| | |
|---|---|
| Cremophor RH 40 ® | 9.6 g (48%), |
| corn-oil-mono-di-tri-glycerides | 5.8 g (29%), |
| propylene glycol | 3.8 g (19%), |
| compound of formula I | 0.8 g (4%). |

This solution is prepared freshly before use.

What is claimed is:

1. A compound of the formula I

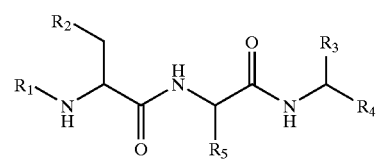

wherein

R$_1$ is unsubstituted or substituted aryl; arylalkylcarbonyl, wherein the aryl moiety is unsubstituted or substituted; unsubstituted or substituted heterocyclyl; or heterocyclylalkylcarbonyl, wherein the heterocyclyl moiety is unsubstituted or substituted;

R$_2$ is unsubstituted or substituted aryl or unsubstituted or substituted heteroaryl;

R$_3$ is hydrogen, unsubstituted or substituted aryl or alkyl which is unsubstituted or substituted by
  unsubstituted or substituted cycloalkyl,
  unsubstituted or substituted aryl, or
  unsubstituted or substituted heteroaryl comprising at least one nitrogen atom;

R$_4$ is a moiety of the formula IA,

wherein A$_1$ and A$_2$ are hydroxy or substituted hydroxy, or together with the binding boron atom and the two binding oxygen atoms form a ring of the formula IA*,

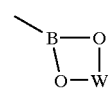

wherein W is alkylene, substituted alkylene, unsubstituted or substituted cycloalkylene, unsubstituted or substituted bicycloalkylene or unsubstituted or substituted tricycloalkylene;

and R$_5$ is unsubstituted or substituted alkyl, unsubstituted or substituted aryl, unsubstituted or substituted heterocyclyl, or unsubstituted or substituted cycloalkyl;

or a salt thereof.

2. A compound of the formula I according to claim 1, wherein the stereochemistry is as depicted in formula I*

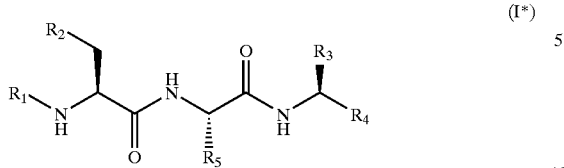

(I*)

wherein the shown configuration represents the absolute configuration and wherein $R_1$, $R_2$, $R_3$, $R_4$ and $R_5$ are as defined for formula I in claim 1,
or a salt thereof.

3. A compound of the formula I according to claim 1, wherein
$R_1$ is either substituted aryl-lower alkylcarbonyl or unsubstituted or substituted aryl,
$R_2$ is substituted aryl or unsubstituted or substituted heterocyclyl,
$R_3$ is lower alkyl, unsubstituted or substituted aryl or lower alkyl which is substituted by unsubstituted or substituted aryl,
$R_4$ is a moiety of the formula IA wherein $A_1$ and $A_2$ are hydroxy, lower alkyloxy, aryloxy with unsubstituted or substituted aryl or cycloalkyloxy with unsubstituted or substituted cycloalkyl, or wherein $A_1$ and $A_2$, together with the binding boron atom and the two binding oxygen atoms form a ring of the formula IA* wherein W is unsubstituted or substituted lower alkylene bound via two different carbon atoms that are spatially nearby or vicinal, especially in vicinal or, relatively to each other, in "1,3"-position, and
$R_5$ is lower alkyl,
or a salt thereof.

4. A compound of the formula I according to claim 1, wherein
$R_1$ is phenyloxyphenyl-lower alkylcarbonyl; phenyl-lower alkoxyphenyl-lower alkylcarbonyl; pyridyloxyphenyl-lower alkylcarbonyl; phenyl-lower alkylcarbonyl substituted by lower alkoxy, halogen, halogen-lower alkyl, or unsubstituted or substituted phenyl or naphthyl, wherein in both cases the substituents if present are independently one or more, especially one to three, substituents selected from the group consisting of lower alkyl, hydroxy, lower alkoxy, lower alkanoyloxy, carboxy, lower alkoxycarbonyl, formyl, lower alkanoyl, amino, N-lower alkylamino, N,N-di-lower alkylamino, mercapto, sulfo, lower alkyl-thio, carbamoyl, N-lower alkyl-carbamoyl; N,N-di-lower alkyl-carbamoyl, phenyl, naphthyl, pyridyl, cyano and nitro, more preferably lower alkoxy;
$R_2$ is phenyl substituted by one or more moieties independently selected from the group consisting of hydroxy, lower alkoxy, halogen, and halogen-lower alkyl;
$R_3$ is lower alkyl, isobutyl, phenyl or phenyl substituted by one or more, up to three substituents independently selected from the group consisting of hydroxy, lower alkoxy, halogen, and halogen-lower alkyl;
$R_4$ is —B(OH)$_2$ or 2,9,9-trimethyl-3,5-dioxa-4-bora-tricyclo[6.1.1.0$^{2,6}$]dec-4-yl; (1S,2S,6R,8S)-2,9,9-trimethyl-3,5-dioxa-4-bora-tricyclo[6.1.1.0$^{2,6}$]dec-4-yl; and
$R_5$ is lower alkyl;
or a salt thereof.

5. A compound of formula I according to claim 1, wherein
$R_1$ is phenyloxyphenylacetyl, benzyloxyphenylacetyl, pyridyloxyphenylacetyl, biphenylyl, pyridylphenyl, lower alkylphenyl or substituted phenylpropionyloxy wherein the phenyl substituents are up to three substituents independently selected from the group consisting of methoxy; fluoro, chloro and trifluoromethyl;
$R_2$ is phenyl substituted with up to three methoxy substituents, especially 2,3,4-trimethoxyphenyl or 3,4,5-trimethoxyphenyl;
$R_3$ is isobutyl or phenyl that is unsubstituted or substituted with up to three moieties independently selected from hydroxy, fluoro and methoxy;
$R_4$ is (1S,2S,6R,8S)-2,9,9-trimethyl-3,5-dioxa-4-bora-tricyclo[6.1.1.0$^{2,6}$]dec-4-yl or —B(OH)$_2$; and
$R_5$ is isopropyl:
or a salt thereof.

6. A compound of formula I according to claim 1, wherein
$R_1$ is biphenylyl, lower alkyl-phenyl, phenyl-lower alkyl-carbonyl, phenoxy-phenyl-lower alkyl-carbonyl, phenyl-lower alkoxy-phenyl-lower alkyl-carbonyl or pyridyl-phenyl;
$R_2$ is either phenyl substituted by 1 to 3 lower alkoxy radicals or phenyl-lower alkoxy-phenyl;
$R_3$ is lower alkyl or phenyl-lower alkyl;
$R_4$ is 4,4,5,5-tetramethyl-[1,3,2]dioxaborolan-2-yl, (1S, 2S,6R8S)-2,9,9-trimethyl-3,5-dioxa-4-bora-tricyclo[6.1.1.0$^{2,6}$]dec-4-yl or —B(OH)$_2$; and
$R_5$ is lower alkyl;
or a salt thereof.

7. A compound of formula I according to claim 1 selected from the group consisting of
(R)-1-{(S)-2-[(S)-2-(biphenyl-3-ylamino)-(3-(3,4,5-trimethoxy-phenyl)-propionylamino]-3-methyl-butyrylamino}-3-methyl-butylboronic acid,
(R)-3-methyl-1-{(S)-3-methyl-2-[(S)-2-[2-(3-phenoxy-phenyl)-acetylamino]-3-(2,3,4-trimethoxy-phenyl)-propionylamino]-butyrylamino}-butylboronic acid and
(R)-3-methyl-1-{(S)-3-methyl-2[(S)-2-(3-phenyl-propionylamino)-3-(2,3,4-trimethoxy-phenyl)-propionylamino]-butyrylamino}-butylboronic acid,
or a pharmaceutically acceptable salt thereof.

8. A compound of formula I according to claim 1 selected from the group consisting of
(S)-2-[(S)-2-(biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide,
(S)-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-[2-(3-phenoxy-phenyl)-acetylamino]-3-(2,3,4-trimethoxy-phenyl)-propionylamino]-butyramide, and
(S)-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-(3-phenyl-propionyl-amino)-3-(2,3,4-trimethoxy-phenyl)-propionylamino]-butyramide,
or a pharmaceutically acceptable salt thereof.

9. A compound of formula I according to claim 1 selected from the group consisting of
(R)-1-{(S)-2-[(S)-2-(biphenyl-3-ylamino)-3-(4-methoxy-phenyl)-propionylamino]-3-methyl-butyrylamino}-3-methyl-butylboronic acid,
(R)-1-{(S)-2-[(S)-2-(biphenyl-3-ylamino)-3-(3,4-dimethoxy-phenyl)-propionylamino]-3-methyl-butyrylamino}-3-methyl-butylboronic acid, (R)-1-{(S)-2-[(S)-2-(3-isopropyl-phenylamino)-3-(3,4,5-trimethoxy-phenyl)-propionylamino]-3-methyl-butyrylamino}-3-methyl-butylboronic acid, (R)-3-methyl-1-{(S)-3-methyl-2-[(S)-2-(3-pyridin-2-yl-phenylamino)-3-(3,4,5-trimethoxy-phenyl)-propionylamino]-butyrylamino}-butylboronic acid, (R)-1-{(S)-2-[(S)-2-(biphenyl-3-ylamino)-3-(2,3,4-trimethoxy-phenyl)-propionylamino]-3-methyl-butyrylamino}-3-methyl-butylboronic acid, (R)-1-{(S)-2-[(S)-3-(4-benzyloxy-phenyl)-2-(biphenyl-3-ylamino)-propionylamino]-3-methyl-butyrylamino}-3-methyl-butylboronic acid, (R)-1-{(R)-2-[(S)-2-(biphenyl-3-ylamino)-3-(3,4,5-trimethoxy-phenyl)-propionylamino]-3-methyl-butyrylamino}-3-methyl-butylboronic acid, (R)-1-{(S)-2-[(R)-2-(biphenyl-3-ylamino)-3-(3,4,5-trimethoxy-phenyl)-propionylamino]-3-methyl-butyrylamino}-3-methyl-butylboronic acid, 1-{(S)-2-[(S)-2-(biphenyl-3-ylamino)-3-(3,4,5-trimethoxy-phenyl)-propionylamino]-3-methyl-butyrylamino}-3-methyl-butylboronic acid, (R)-1-((S)-2-{(S)-3-(3,4-dimethoxy-phenyl)-2-[2-(3-phenoxy-phenyl)-acetylamino]-propionylamino}-3-methyl-butyrylamino)-3-methyl-butylboronic acid, (R)-3-methyl-1-{(S)-3-methyl-2-[(S)-2-[2-(3-phenoxy-phenyl)-acetylamino]-3-(3,4,5-trimethoxy-phenyl)-propionylamino]-butyrylamino}-butylboronic acid, (R)-1-((S)-2-{(S)-3-(4-benzyloxy-phenyl)-2-[2-(3-benzyloxy-phenyl)-acetylamino]-propionylamino}-3-methyl-butyrylamino)-3-methyl-butylboronic acid, (R)-1-{(S)-2-[(S)-2-(biphenyl-3-ylamino)-3-(3,4,5-trimethoxy-phenyl)-propionylamino]-4-methyl-pentanoylamino}-3-methyl-butylboronic acid, (R)-1-{(S)-2-[(S)-2-(biphenyl-3-ylamino)-3-(3,4,5-trimethoxy-phenyl)-propionylamino]-4-methyl-pentanoylamino}-3-methyl-butylboronic acid, (R)-1-{(S)-2-[(S)-2-(biphenyl-3-ylamino)-3-(4-methoxy-phenyl)-propionylamino]-4-methyl-pentanoylamino}-3-methyl-butylboronic acid, (R)-1-{(S)-2-[(S)-2-(biphenyl-3-ylamino)-3-(3,4,5-trimethoxy-phenyl)-propionylamino]-propionylamino}-3-methyl-butylboronic acid, (R)-1-{(S)-2-[(S)-2-(biphenyl-3-ylamino)-3-(2,3,4-trimethoxy-phenyl)-propionylamino]-propionylamino}-3-methyl-butylboronic acid, (R)-1-{(S)-2-[(S)-2-(biphenyl-3-ylamino)-3-(4-methoxy-phenyl)-propionylamino]-propionylamino}-3-methyl-butylboronic acid, (R)-1-{(S)-2-[(S)-2-(biphenyl-3-ylamino)-3-(3,4-dimethoxy-phenyl)-propionylamino]-propionylamino}-3-methyl-butylboronic acid, (R)-1-{(S)-2-[(S)-2-(3-isopropyl-phenylamino)-3-(3,4,5-trimethoxy-phenyl)-propionylamino]-propionylamino}-3-methyl-butylboronic acid, (R)-3-methyl-1-{(S)-2-[(S)-2-(3-phenyl-propionylamino)-3-(2,3,4-trimethoxy-phenyl)-propionylamino]-propionylamino}-butylboronic acid, (R)-1-{(S)-2-[(S)-2-(biphenyl-3-ylamino)-3-(3,4,5-trimethoxy-phenyl)-propionylamino]-3-methyl-butyrylamino}-2-phenyl-ethylboronic acid, and (R)-1-{(S)-2-[(S)-2-(biphenyl-3-ylamino)-3-(4-methoxy-phenyl)-propionylamino]-3-methyl-butyrylamino}-2-phenyl-ethylboronic acid, or a pharmaceutically acceptable salt thereof.

10. A compound of formula I according to claim 1 selected from the group consisting of (S)-2-[(S)-2-(biphenyl-3-ylamino)-3-(4-methoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-2-[(S)-2-(biphenyl-3-ylamino)-3-(3,4-dimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-2-[(S)-(3-isopropyl-phenylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-(3-pyridin-2-yl-phenylamino)-3-(3,4,5-trimethoxy-phenyl)-propionylamino]-butyramide, (S)-2-[(S)-2-(biphenyl-3-ylamino)-3-(2,3,4-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-2-[(S)-3-(4-benzyloxy-phenyl)-2-(biphenyl-3-ylamino)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (R)-2-[(S)-2-(biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-2-(biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-2-[(S)-2-(biphenyl-3-ylamino)-3-(3,4,5-trimethoxy-phenyl)-propionylamino]-3-methyl-N-[3-methyl-1-(4,4,5,5-tetramethyl-[1,3,2]dioxaborolan-2-yl)-butyl]-butyramide, (S)-2-{(S)-3-(3,4-dimethoxy-phenyl)-2-[2-(3-phenoxy-phenyl)-acetylamino]-propionylamino}-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-[2-(3-phenoxy-phenyl)-acetylamino]-3-(3,4,5-trimethoxy-phenyl)-propionylamino]-butyramide, (S)-2-{(S)-3-(4-benzyloxy-phenyl)-2-[2-(3-benzyloxy-phenyl)-acetylamino]-propionylamino}-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide, (S)-2-[(S)-2-(biphenyl-3-ylamino)-3-(3,4,5-trimethoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide, (S)-2-[(S)-2-(biphenyl-3-ylamino)-3-(3,4-dimethoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide, (S)-2-[(S)-2-(biphenyl-3-ylamino)-3-(4-methoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide, (S)-2-(biphenyl-3-ylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(3,4,5-trimethoxy-phenyl)-propionamide, (S)-2-(biphenyl-3-ylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(2,3,4-trimethoxy-phenyl)-propionamide, (S)-2-(biphenyl-3-ylamino)-3-(4-methoxy-phenyl)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-propionamide, (S)-2-(biphenyl-3-ylamino)-3-(3,4-dimethoxy-phenyl)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-propionamide, (S)-2-(3-isopropyl-phenylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(3,4,5-trimethoxy-phenyl)-propionamide, (S)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}2-(3-phenyl-propionylamino)-3-(2,3,4-trimethoxy-phenyl)-propionamide, (S)-2-[(S)-2-(biphenyl-3-ylamino)-3-(3,4,5-trimethoxy-phenyl)-propionylamino]-3-methyl-N-[(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-butyramide, and (S)-2-[(S)-2-(biphenyl-3-ylamino)-3-(4-methoxy-phenyl)-propionylamino]-3-methyl-N-[(R)-2-phenyl-1-((1S,2S,6R,8S)-2,9,9-trimethyl-3,5-dioxa-4-bora-tricyclo[6.1.1.0$^{2,6}$]dec-4-yl)-ethyl]-butyramide, or a pharmaceutically acceptable salt thereof.

11. A compound of formula I according to claim 1 which is (R)-1-{(S)-2-[(S)-2-(biphenyl-3-ylamino)-3-(4-methoxy-phenyl)-propionylamino]-3-methyl-butyrylamino}-3-methyl-butylboronic acid,
or a pharmaceutically acceptable salt thereof.

12. A compound of formula I according to claim 1 which is (R)-1-((S)-2-{(S)-3-(3,4-dimethoxy-phenyl)-2-[2-(3-phenoxy-phenyl)-acetylamino]-propionylamino}-3-methyl-butyrylamino)-3-methyl-butylboronic acid,
or a pharmaceutically acceptable salt thereof.

13. A pharmaceutically acceptable salt of a compound of formula I according to claim 1.

14. A pharmaceutical composition comprising a compound of formula I according to claim 1 or a pharmaceutically acceptable salt of such a compound together with a pharmaceutically acceptable carrier.

15. A pharmaceutical composition for the treatment of a proliferative disease in warm-blooded animals, comprising, in a dose effective against said disease, a compound of formula I according to claim 1, or a pharmaceutically acceptable salt of such a compound, together with a pharmaceutically acceptable carrier, wherein the proliferative disease is selected from, colon tumors, breast tumors, lung tumors and prostate tumor.

16. A method of treating warm-blooded animals, which comprises administering to such a warm-blooded animal suffering from a proliferative disease a therapeutically effective amount of a compound of formula I according to claim 1 or of a pharmaceutically acceptable salt of such a compound, wherein the proliferative disease is selected from, colon tumors, breast tumors, lung tumors and prostate tumor.

17. A process for the preparation of a compound of formula I according to claim 1 or of a salt of such a compound, comprising
a) reacting a dipeptide analogue of the formula II,

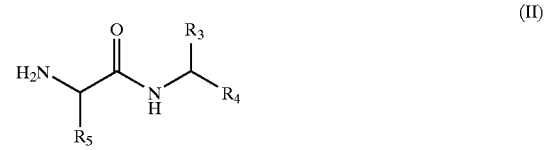

wherein $R_3$, $R_4$ and $R_5$ have the meanings as defined in claim 1, with a carbonic acid of the formula III,

or a reactive derivative thereof, wherein $R_1$ and $R_2$ have the meanings as defined in claim 1;
b) optionally reacting readily removable protecting groups with functional groups on a compound of formula II and/or III, where the functional groups reacted are not groups participating in the reaction of step a);
c) removing protecting groups from the compound resulting from step b); and
d) optionally converting the resulting compound of formula I into another compound of formula I, converting an obtained free compound of formula I into a salt, converting an obtained salt of a compound of formula I into a different salt or into its free form, and/or separating a mixture of isomeric compounds of formula I into the individual isomers.

18. A process for the preparation of a compound of formula I according to claim 1 or of a salt of such a compound, wherein $R_1$ is arylalkylcarbonyl or heterocyclylalkylcarbonyl and the other moieties $R_2$ to $R_5$ have the meanings as defined in claim 1, comprising
a) reacting an amino compound of the formula IV,

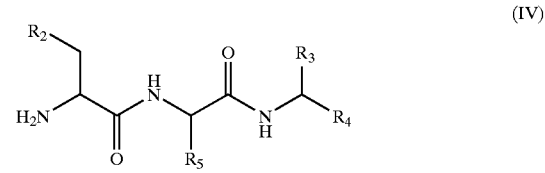

with a carbonic acid of the formula V,

or a reactive derivative thereof, wherein $R_1$ is arylalkylcarbonyl or heterocyclylalkylcarbonyl;
b) optionally reacting readily removable protecting groups with functional groups on a compound of formula II and/or III, where the functional groups reacted are not groups participating in the reaction of step a);

c) removing protecting groups from the compound resulting from step b); and d) optionally converting the resulting compound of formula I into another compound of formula I, converting an obtained free compound of formula I into a salt, converting an obtained salt of a compound of formula I into a different salt or into its free form, and/or separating a mixture of isomeric compounds of formula I into the individual isomers.

* * * * *